United States Patent [19]

Or et al.

[11] Patent Number: 5,663,148

[45] Date of Patent: Sep. 2, 1997

[54] ANAPHYLATOXIN RECEPTOR LIGANDS CONTAINING LIPOPHILIC RESIDUES

[75] Inventors: Yat Sun Or; Jay R. Luly, both of Libertyville, Ill.

[73] Assignee: Abbott Laboratories, Abbott Park, Ill.

[21] Appl. No.: 274,060

[22] Filed: Jul. 12, 1994

[51] Int. Cl.$^6$ .............. A61K 38/00; C07K 5/00; C07K 7/00; C07K 17/00

[52] U.S. Cl. .............. 514/17; 514/18; 514/16; 530/328; 530/329; 530/330; 530/331

[58] Field of Search ............ 514/15, 16, 17, 514/18; 530/328, 329, 330, 331

[56] References Cited

U.S. PATENT DOCUMENTS 5,223,485  6/1993  Kawai et al. .............. 514/16

FOREIGN PATENT DOCUMENTS 9407815  4/1994  WIPO .
9407518  4/1994  WIPO .............. A61K 37/02

OTHER PUBLICATIONS

Gerard et al., *Journal of Immunology*, vol. 127, No. 5, Nov. 1981, pp. 1978–1982.

Ember et al., *Journal of Immunology*, vol. 148, No. 10, May 15, 1992, pp. 3165–3173.

*Primary Examiner*—Avis M. Davenport
*Attorney, Agent, or Firm*—Jerry F. Janssen

[57] ABSTRACT

Oligopeptide compounds or oligopeptide analague compounds of the formula, A-B-D-E-G-J-L-M-N($R^4$)Arg-OH, which are ligands for the anaphylatoxin receptor and are useful in the treatment of inflammatory disease states, as well as anaphylatoxin receptor ligand compositions and a method for modulating anaphylatoxin activity.

7 Claims, No Drawings

ANAPHYLATOXIN RECEPTOR LIGANDS CONTAINING LIPOPHILIC RESIDUES

TECHNICAL FIELD

This invention relates to organic compounds that modulate C5a anaphylatoxin activity and to methods and compositions for modulating C5a anaphylatoxin activity in human and animal hosts in need of such treatment.

BACKGROUND OF THE INVENTION

A wide variety of conditions, including infection by bacteria, viruses or fungi, infiltration by cancer cells, allergic or autoimmune disorders and physically- or chemically-induced trauma, cause inflammatory responses in humans. In all of these diseases and conditions in man and in most mammals, activation of the complement system (a set of proteins, regulatory factors and proteolytic enzymes) via either the classical or the alternative pathway, results in the generation of biologically-active peptides which serve to amplify and exacerbate the resulting inflammation.

The most active peptide, anaphylatoxin C5a, a 74-amino acid polypeptide which is released during the activation of serum complement proteins, is generated by cleavage of the alpha-chain of native C5 at a specific site by convertases (proteolytic enzymes) of the blood complement system, as well as by enzymes of the coagulation system. C5a exists in vivo in two biologically-active forms. Once it is liberated from C5, the carboxyl-terminal arginine of C5a is rapidly removed by carboxypeptidase-N, leaving the des-Arg derivative. Although C5a des-Arg is less active than C5a, both are potent inflammatory mediators at concentrations likely to be generated in vivo (Fernandez, H. N.; Henson, P. M.; Otani, A. and Hugli, T. E., *J. Immunol.* 1978, 120, 109). Together, these peptides, along with C3a, C4a, and their des-Arg degradation products, collectively described herein as anaphylatoxin, are capable of triggering diverse inflammatory reactions (Hugli, T. E. and Muller-Eberhard, H. J., *Adv. Immunol.* 1978, 26, 1–53; Hugli, T. E., *Crit. Rev. Immunol* 1981, 1, 321–366; Frank, M. M. and Fries, L. F., *Immunol. Today* 1991, 12, 322–326; Goldstein, I. M. in Inflammation: *Basic Principles and Clinical Correlates* 1992, (Gallin, J. I.; Goldstein, I. M. and Snyderman, R., eds), pp 63–80, Raven Press; and Hugli, T. E., *Stinger Semin. Immunopathol.* 1984, 7, 193–219). C5a is believed to play a major role as a potent inflammatory mediator by its additional activities in recruiting and stimulating inflammatory leukocyctes.

Once liberated from its parent molecule, C5a interacts with specific membrane receptors present on white blood cells including polymorphonuclear leukeocytes (PMNL), monocytes, basophils, and eosinophils, as well as with tissue resident cells such a macrophages and mast cells. Among the various cell types, the neutrophil response to C5a is the best defined. Chenoweth and Hugli (Chenoweth, D. E. and Hugli, T. E., *Proc. Nat. Acad. Sci. U.S.A.* 1978, 75, 3943–3947) have shown that binding of human C5a to intact polymorphonuclear leukocytes is saturable and specific, and effected the induction of a cellular response. Cell surface receptors specific for C5a have been demonstrated on the neutrophil (Huey, R. and Hugli, T. E., *J. Immunol.* 1985, 135, 2063–2068; and Rollins, T. E. and Springer, M. S., *J. Bio. Chem.* 1985, 260, 7157–7160), and the ligand-receptor interaction has been shown to promote human polymorphonuclear leukocyte (PMNL) migration in a directed fashion (chemotaxis) (Frank, M., Rev. Infectious Diseases 1979, 1(3), 483–501), adherence, oxidative burst, and granular enzyme release from these cells (Hugli, T. E., *Springer Semin. Immunopathol.* 1984, 7, 193–219). The interaction of C5a with PMN and other target cells and tissues results in increased histamine release, vascular permeability, smooth muscle contraction, and an influx into tissues of inflammatory cells, including neutrophils, eosinophils, and basophils (Hugli, T. E., *Springer Semin. Immunopathol.* 1984, 7, 193–219).

C5a may also be important in mediating inflammatory effects of phagocytic mononuclear cells that accumulate at sites of chronic inflammation (Allison, A. C.; Ferluga, J.; Prydz, H. and SCherlemmer, H. U., *Agents and Actions* 1978, 8, 27). C5a and C5a des-Arg can induce cherootaxis in monocytes (Ward, P. A., *J. Exp. Med.* 1968, 128, 1201; and Snyderman, R.; Shin, H. S. and Dannenberg, A. C., *J. ImmunoL* 1972, 109, 896) and cause them to release lysosomal enzymes (McCarthy, K. and Henson, P. S., J. Immunol. 1979, 123, 2511) in a manner analogous to the neutrophil responses elicited by these agents. In addition, recent studies suggest that C5a may have an immunoregulatory role by enhancing antibody particularly at sites of inflammation (Morgan, E. L.; Weigle, W. O. and Hugli, T. E., *J. Exp. Med.* 1982, 155, 1412; Weigle, W. O.; Morgan, E. L.; Goodman, M. G.; Chenoweth, D. E. and Hugli, T. E., *Federation Proc.* 1982, 41, 3099; and Morgan, E. L.; Weigle, W. O. and Hugli, T. E., *Federation Proc.* 1984, 43, 2543).

C5a and C5a des-Arg additionally play important roles in host defenses against bacterial infections and possibly in the mediation of some pathologic lesions such as the leukocyte infiltration seen in the lungs during acute respiratory distress syndrome. This mechanism seems to play a role in different pathological situations like pulmonary distress during hemodialysis, leukophoresis, cardiopulmonary bypass, and in acute myocardial infarction. Complement activation has been postulated to play an important pathological role in rheumatoid arthritis, serum sickness, systemic lupus erythematosus, ulcerative colitis, and forms of hepatic cirrhosis, chronic hepatitis, and glomerulonephitis, in certain shock states, during hemodialysis, and cardiopulmonary bypass, acute pancreatitis, myocardial infarction (which may be worsened by C5a-induced leuko-embolization following the interaction of complement with atheromatous plaques), asthma, bronchoconstriction, some auto-allergic diseases, transplant rejection, and post-viral encephalopathies.

Thus, the search for specific C5a receptor antagonists to bind to and block the anaphylatoxin receptor and thus prevent or reduce anaphylatoxin-mediated inflammation, and C5a receptor agonists to assist the body in building its defense mechanisms against invasion by infectious agents and malignancy, as well as possibly influencing the immunoregulatory effects of anaphylatoxin, has been an active and ongoing process in recent years because of its therapeutic implications.

The search has centered on the C5a receptor binding affinity of compounds, based on the results of numerous studies which support the conclusion of a strong correlation between in vitro binding of a compound at the C5a receptor and its ability to modulate the in vitro and in vivo response of those cells to which C5a also binds, that is, to modulate C5a activity (Gerard, C., et al., *J. ImmunoL* 1981, 127, 1978–1982; Johnson, R. J. and Chenoweth, D. E., *J. Biol Chem.*, 1985, 260, 10339–10345; Swerlick, R. A., et al., *J. Immunol.*, 1988, 140, 237–238; and Mollison, K. W., et al., *Proc. Natl. Acad. Sci. USA,* 1989, 86, 292–296). "It is precisely the receptor-ligand interactions that classify anaphylatoxins as local hormones and cellular reactions to ligand binding that escalates the functional impact of these complement factors to systemic proportions" (Hugli, T. E., Springer Semin. Immunopathol. 1984, 7, 195).

Although most studies have addressed the in vitro properties of human C5a and C5a receptor binding analogues, in vivo studies with human volunteers showed that human C5a des Arg-74 can elicit inflammatory responses in human skin, but C5a des Arg-74 was less potent than native C5a (Swerlick et al, op.cit.). The difference between native C5a and C5a des Arg-74 activity in vivo is consistent with the lower in Vitro C5a receptor binding afffinity that was reported for C5a des Arg-74 (Gerard et al., op.cit.).

Once the identity of a compound which binds to the C5a receptor has been made, the methods are well known to determine whether the compound is functioning as a C5a agonist or antagonist (Hugli, T., "The Structural Basis for Anaphylatoxin and Chemotactic Functions of C3a, C4a and C5a", Chapter 4, pages 321–366 in *Critical Reviews in Immunology, 1*, CRC Press, Boca Raton, Fla. (1981)).

Thus, the novel antagonists and agonists of the present invention represent useful agents in this field. The possible involvement of anaphylatoxin in a wide range of diseases, as indicated by the examples above, suggests that anaphylatoxin receptor ligands could have clinical applications for the treatment and prevention of serious pathological conditions.

Kawai et al., U.S. Pat. No. 5,223,485, issued Jun. 29, 1993, discloses and claims C5a receptor antagonists having 7–12 amino acid residues, which neither anticipate nor suggest the compounds of the instant invention. The present invention's unique C-terminal dipeptide fragment of "homo-homoarylalanyl" (that has a three atom chain between the aryl moiety and the asymmetric carbon atom) at the M position which is coupled to the α-amino group of the C-terminal arginine residue, among other differences, clearly distinguishes the novel compounds of the present invention.

SUMMARY OF THE INVENTION

The present invention provides C5a anaphylatoxin activity-modifying compounds of the formula, A-B-D-E-G-J-L-M-N($R^4$)Arg-OH, or pharmaceutically-acceptable salts thereof.

In the generic formula given above, the groups B, D, E, G, J, and L may individually be absent or may represent naturally-occuring or modified amino acids, including peptides in which various peptide bonds have been N-alkylated or reduced.

The present invention also relates to a method for modulating C5a anaphylatoxin activity in a mammal in need of such treatment, comprising administering to such mammal a therapeutically-effective amount of a compound of the above description.

The invention further relates to C5a anaphylatoxin-modulating compositions comprising a pharmaceutical carrier and a therapeutically-effective amount of a compound of the above description.

DETAILED DESCRIPTION

The present invention is directed to oligopeptides containing as few as three areinc acid residues, as well as to peptidomimetic compounds (i.e., compounds which mimic the activity of peptides), in which certain groups replace the co-carbon, carbonyl group, and amide-nitrogen group of the individual amino acids in oligopeptides, which are also actively bound by C5a receptors, thus beneficially impeding activation of C5a, the most active of a class of biologically-active peptides which serve to amplify and exacerbate inflammation.

The chemical structures of the compounds of the present invention are best understood by reference to the following structural formula in which it is understood that the segments are joined serially at the free valence bonds to form the compound, A-B-D-E-G-J-L-M-N($R^4$)Arg -OH (I)

where:

A is $R^1$–$R^2$, hydrogen, $C_1$–$C_8$-alkyl, aryl-$C_1$–$C_6$-alkyl, amino-$C_1$–$C_8$-alkyl, guanidino-$C_1$–$C_8$-alkyl, amino-$C_1$–$C_8$-alkyl-C(O)-or guanidino-$C_1$–$C_8$-alkyl-C(O)-, with the proviso that when none of the optionally-present residues, B, D, E, G and J, is absent, A is hydrogen or methyl;

B is absent or —N($R_4$)—C($R^5$)($R^6$)—$R^3$—;

D is absent or —N($R^4$)—C($R^7$)($R^8$)—$R^3$—;

E is absent or —N($R^4$)—C($R^9$)($R^{10}$)—$R^3$—, or $R^{20}$, or when either residue B or residue D is absent, $R^{19}$;

G is absent or —N($R^4$)—C($R^{11}$)($R^{12}$)—$R^3$—;

J is absent or —N($R^{21}$)—C($R^{13}$)($R^{14}$)—$R^3$—, or $R_{20}$—;

L is —N($R^4$)—C($R^{15}$)($R^{16}$)—C(O)—; and

M is —N($R^4$)—C($R^{17}$)($R^{18}$)—C(O)—, wherein $R^1$ is $C_1$–$C_8$-alkyl, aryl, aryl-$C_1$–$C_6$-alkyl, amino-$C_1$–$C_8$-alkyl, (heterocyclic)-$C_1$–$C_6$-alkyl or hydrogen, with the proviso that when $R^2$ is >$SO_2$, then $R^1$ may not be hydrogen;

$R^2$ is >C=O, >$CH_2$, —NH—C(O)— or >$SO_2$;

$R^3$ is >C=O, >$CH_2$, or —$CH_2$—C(O)—;

$R^4$ is hydrogen, $C_1$–$C_8$-alkyl or aryl —$C_1$–$C_6$-alkyl;

$R^5$, $R^7$, $R^9$, $R^{11}$, $R^{13}$, $R^{15}$, and $R^{17}$ are independently hydrogen or $C_1$–$C_8$-alkyl;

$R^6$ is hydrogen, $C_1$–$C_8$-alkyl, aryl, aryl-$C_1$–$C_6$-alkyl or (heterocyclic)-$C_1$–$C_6$-alkyl;

$R^8$ is hydrogen, $C_1$–$C_8$-alkyl, amino-$C_1$–$C_8$-alkyl, or guanidino-$C_1$–$C_8$-alkyl;

$R^{10}$ is selected from the group consisting of hydrogen, $C_1$–$C_8$-alkyl, aryl, aryl-$C_1$–$C_6$-alkyl, amino-$C_1$–$C_8$-alkyl, amino(cyclo-$C_3$–$C_6$-alkyl), amido-$C_1$–$C_8$-alkyl, hydroxy-$C_1$–$C_8$-alkyl, guanidino-$C_1$–$C_8$-alkyl and carboxy-$C_1$–$C_8$-alkyl;

$R^{12}$ is selected from the group consisting of hydrogen, sulfhydryl-$C_1$–$C_8$-alkyl, (thio-$C_1$–$C_8$-alkoxy)-$C_1$–$C_8$-alkyl, $C_1$–$C_8$-alkyl, aryl, aryl-$C_1$–$C_6$-alkyl, (cyclo-$C_3$–$C_6$-alkyl)-$C_1$–$C_8$-alkyl and (heterocyclic)-$C_1$–$C_6$-alkyl;

$R^{14}$ is selected from the group consisting of hydrogen, $C_1$–$C_8$-alkyl, amino-$C_1$–$C_8$-alkyl, aryl, aryl-$C_1$–$C_6$-alkyl, (cyclo-$C_3$–$C_6$-alkyl)-$C_1$–$C_8$-alkyl, (carboxamido)-$C_1$–$C_8$-alkyl and (heterocyclic)-$C_1$–$C_6$-alkyl;

$R^{16}$ is hydrogen, $C_1$–$C_8$-alkyl, aryl, aryl-$C_1$–$C_6$-alkyl, (cyclo-$C_3$–$C_6$-alkyl)-$C_1$–$C_8$-alkyl or (heterocyclic)-$C_1$–$C_6$-alkyl;

$R^{18}$ is selected from the group consisting of (a) —$(CH_2)_3$-(aryl), (b) —$CH_2$—W—$CH_2$-(aryl), where W is selected from >O, >S, and >N—R, where R is hydrogen or $C_1$–$C_8$-alkyl, and (c) —CH₂—CH₂—W—(aryl), where W is as defined above;

R¹⁹ is

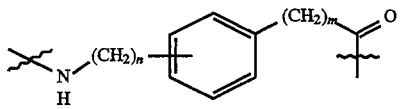

where m and n are integers independently selected from 0, 1 and 2;

R²⁰ is

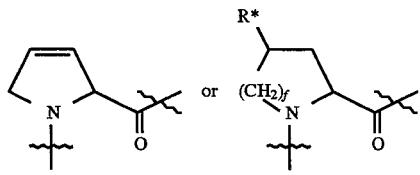

where f is 1 or 2, R* is hydrogen, hydroxy, $C_1$–$C_8$-alkoxy or aryl-$C_1$–$C_8$-alkoxy; and
R²¹ is hydrogen or $C_1$–$C_8$-alkyl.

In one embodiment of the present invention A-B-D-E-G-J-L-M-N(R⁴)Arg—OH may be represented as:

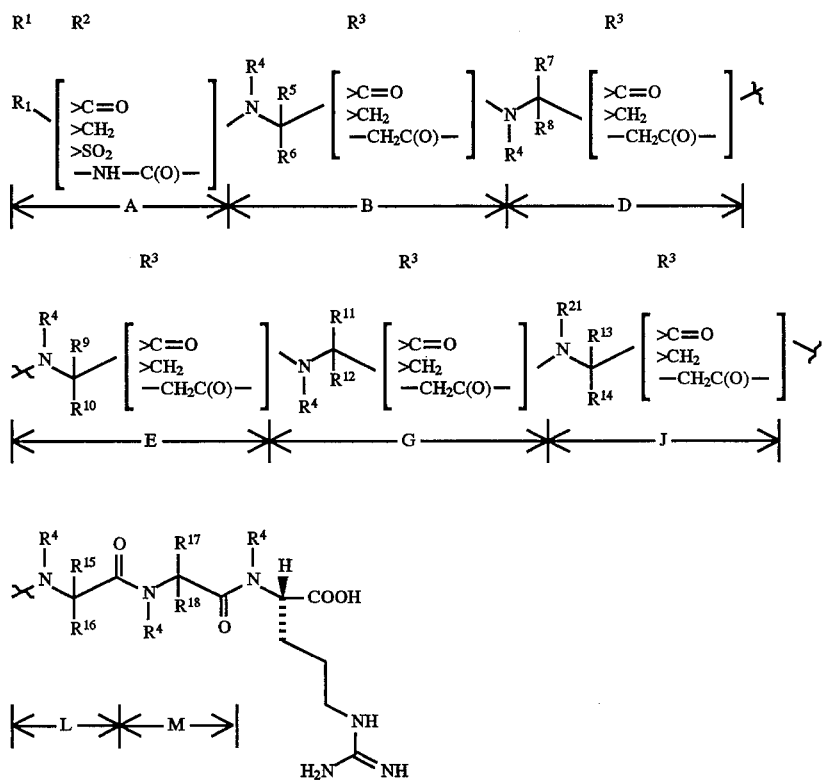

Preferred classes of compounds of the present invention are those in which R⁴ and R²¹ are independently hydrogen or methyl, and/or R³ is >C=O or >CH₂.

One class of preferred compounds of the present invention is that in which M is 2-Amino-5-phenylpentanoyl, particularly when the chirality of M is R.

In preferred embodiments of the present invention, R⁴ and R²¹ are hydrogen, R³ is carbonyl, and R¹⁸ is —(CH₂)₃-phenyl, —CH₂—S—CH₂-phenyl, or —CH₂—O—CH₂-phenyl.

Representative examples of compounds where M is 2-Amino-5-phenylpentanoyl} include the following compounds, as well as pharmaceutically-acceptable salts thereof:

H-Phenylalanyl-Lysyl-Prolyl-{(2S)-2-Amino-3-cyclohexylpropanoyl}-Alanyl-Leucyl-{(R/S)-2-Amino-5-phenylpentanoyl}-Arginyl-OH;

H-Phenylalanyl-Lysyl(N-epsilon-Cbz)-Prolyl-{(2S)-2-Amino-3-cyclohexylpropanoyl}-Alanyl-Leucyl-{(R/S)-2-Amino-5-phenylpentanoyl}-Arginyl-OH;

H-Phenylalanyl-Lysyl-Alanyl-{(2S)-2-Amino-3-cyclohexylpropanoyl}-Alanyl-DPhenylalanyl-{(R/S)-2-Amino-5-phenylpentanoyl}-Arginyl-OH;

H-Phenylalanyl-Lysyl-Alanyl-{(2S)-2-Amino-3-cyclohexylpropanoyl}-Alanyl-DPhenylalanyl-{( R/S)-2-Amino-5-phenylpentanoyl}-Arginyl-OH;

H-Lysyl-Glycyl-{(2S)-2-Amino-3-cyclohexylpropanoyl}-Glycyl-Leucyl-{(R/S)-2-Amino-5-phenylpentanoyl}-Arginyl-OH;

H-Phenylalanyl-Lysyl-Alanyl-{(2S)-2-Amino-3-cyclohexylpropanoyl}-Alanyl-Phenylalanyl-{( R/S)-2-Amino-5-phenylpentanoyl}-Arginyl-OH;

H-Phenylalanyl-Lysyl-Alanyl-{(2S)-2-Amino-3-cyclohexylpropanoyl}-Alanyl-Phenylalanyl-{(R/S)-2-Amino-5-phenylpentanoyl}-Arginyl-OH;

H-{(2S)-2-Amino-3-cyclonexylpropanoyl}-Alanyl-Leucyl-{(R)-2-Amino-5-phenylpentanoyl}-Arginyl-OH;

N-(6-Aminohexanoyl)-Phenylalanyl(N-methyl)-Glycyl-Leucyl-{(R/S)-2-Amino-5-phenylpentanoyl}-Arginyl-OH;

N-(7-Aminoheptanoyl)-{(2S)-2-Amino-3-cyclohexylpropanoyl}-Glycyl-Leucyl(N-methyl)-{(R/S)-2-Amino-5-phenylpentanoyl}-Arginyl-OH;

N-(7-Aminoheptanoyl)-{(2S)-2-Amino-3-cyclohexylpropanoyl}-Glycyl-Leucyl-{(R/S)-2-Amino-5-phenylpentanoyl}(N-methyl)-Arginyl-OH;

N-(6-Aminohexanoyl)-Glycyl-{(2S)-2-Amino-3-cyclohexylpropanoyl}-Alanyl-Leucyl-{(R/S)-2-Amino-5-phenylpentanoyl}-Arginyl-OH;

H-Lysyl-{(2S)-2-Amino-3-cyclohexylpropanoyl}-Glycyl-Leucyl-{(R/S)-2-Amino-5-phenylpentanoyl}-Arginyl-OH;

H-Glycyl-Lysyl-Prolyl-{(2S)-2-Amino-3-cyclohexylpropanoyl}-Alanyl-Leucyl-{(R/S)-2-Amino-5-phenylpentanoyl}-Arginyl-OH;

H-{(2S)-2-Amino-3-cyclohexylpropanoyl}-Glycyl-Leucyl-{(R/S)-2-Amino-5-phenylpentanoyl}-Arginyl-OH;

H-Lysyl-Prolyl-{(2S)-2-Amino-3-cyclohexylpropanoyl}-Alanyl-Leucyl-{(R/S)-2-Amino-5-phenylpentanoyl}-Arginyl-OH;

N-(6-Aminohexanoyl)-{(2S)-2-Amino-3-cyclohexylpropanoyl}-Glycyl-Leucyl-{(R/S)-2-Amino-5-phenylpentanoyl}-Arginyl-OH;

N-(6-Aminohexanoyl)-Prolyl-{(2S)-2-Amino-3-cyclohexylpropanoyl}-Alanyl-Leucyl-{(±)-2-Amino-5-phenylpentanoyl}-Arginyl-OH;

N-(6-Aminohexanoyl)-Prolyl-{(2S)-2-Amino-3-cyclohexylpropanoyl}-Alanyl-Leucyl-{(±)-2-Amino-5-phenylpentanoyl}-Arginyl-OH;

N-(8-Aminocaproyl)-{(2S)-2-Amino-3-cyclohexylpropanoyl}-Glycyl-Leucyl-{(R/S)-2-Amino-5-phenylpentanoyl}-Arginyl-OH;

N-(gamma-Aminobutyryl)-Sarcosinyl-{(2S)-2-Amino-3-cyclohexyl-propanoyl}-Glycyl-Leucyl-{(R/S)-2-Amino-5-phenylpentanoyl}-Arginyl-OH;

N-(6-Aminohexanoyl)-Sarcosinyl-{(2S)-2-Amino-3-cyclohexylpropanoyl}-Alanyl-Leucyl-{(R/S)-2-Amino-5-phenylpentanoyl}-Arginyl—OH;

N-(7-Aminoheptanoyl)-{(2S)-2-Amino-3-cyclohexylpropanoyl}-Glycyl-Leucyl-{(R/S)-2-Amino-5-phenylpentanoyl}-Arginyl-OH;

N-(6-Aminohexanoyl)-Phenylalanyl-Glycyl-Leucyl-{(R/S)-2-Amino-5-phenylpentanoyl}-Arginyl-OH;

N-Methyl-Phenylalanyl-Lysyl-Prolyl-{(2S)-2-Amino-3-cyclohexyl-propanoyl}-Alanyl-Leucyl-{(R/S)-2-Amino-5-phenylpentanoyl}-Arginyl-OH;

N-Methyl-Phenylalanyl-Lysyl-Prolyl-{(2S)-2-Amino-3-cyclohexyl-propanoyl}-Alanyl-Leucyl-{(R/S)-2-Amino-5-phenylpentanoyl}-Arginyl-OH;

N-(5-Aminopentanoyl)-{(2S)-2-Amino-3-cyclohexylpropanoyl}-Glycyl-Leucyl-{(R/S)-2-Amino-5-phenylpentanoyl}-Arginyl-OH;

N-(6-Aminohexanoyl)-{(2S)-2-Amino-3-cyclohexylpropanoyl}-(3-Amino-methylbenzoyl)-{(±)-2-Amino-5-phenylpentanoyl}-Arginyl-OH;

N-(gama-Aminobutyryl)-{(2S)-2-Amino-3-cyclohexylpropanoyl}-Glycyl-Leucyl-{(R/S)-2-Amino-5-phenylpentanoyl}-Arginyl-OH;

H-(4-Pyridyl)alanyl-Lysyl-Prolyl-{(2S)-2-Amino-3-cyclohexylpropanoyl}-Alanyl-Leucyl-{(R)-2-Amino-5-phenylpentanoyl}-Arginyl-OH;

H-Phenylalanyl-Lysyl-Alanyl-{(2S)-2-Amino-3-cyclohexylpropanoyl}-Alanyl-(Indol-3-yl)alanyl-{(R/S)-2-Amino-5-phenylpentanoyl}-Arginyl-OH;

N-(6-Aminohexanoyl)-(2-Thienyl)alanyl(N-methyl)-Glycyl-Leucyl-{(R/S)-2-Amino-5-phenylpentanoyl}-Arginyl-OH; and H-Phenylalanyl-Lysyl-Alanyl-{(2S)-2-Amino-4-(Morpholinyl)butanoyl}-Alanyl-Phenylalanyl-{(R/S)-2-Amino-5-phenylpentanoyl}-Arginyl-OH.

In another embodiment of the present invention, J-L-M taken together is Glycyl-Leucyl-{(R)-2-Amino-5-phenylpentanoyl}, as represented by the following compounds, as well as pharmaceutically-acceptable salts thereof:

N-(3-Phenylpropyl)-Tryptophanyl-Glycyl-Leucyl-{(R)-2-Amino-5-phenylpentanoyl}-Arginyl-OH;

H-Prolyl-{(2S)-2-Amino-3-cyclohexylpropanoyl}-Alanyl-Leucyl-{(R)-2-Amino-5-phenylpentanoyl}-Arginyl-OH;

N-(3-Phenylpropanoyl)-{(2S)-2-Amino-3-cyclohexylpropanoyl}-Glycyl-Leucyl-{(R)-2-Amino-5-phenylpentanoyl}-Arginyl-OH;

N-(Indole-3-acetyl)-Glycyl-Leucyl-{(R)-2-Amino-5-phenylpentanoyl}-Arginyl-OH;

N-(4-Phenylbutyryl)-{(2S)-2-Amino-3-cyclohexylpropanoyl}-Glycyl-Leucyl-{(R)-2-Amino-5-phenylpentanoyl}-Arginyl-OH;

H-{(2S)-2-Amino-3-cyclohexylpropanoyl}(N-Benzyl)-Glycyl-Leucyl-{(R)-2-Amino-5-phenylpentanoyl}-Arginyl-OH;

N-(7-Aminoheptanoyl)-{(2S)-2-Amino-3-cyclohexylpropanoyl}(N-Benzyl)-Glycyl-Leucyl-{(R)-2-Amino-5-phenylpentanoyl}-Arginyl-OH;

N-[(1,2-Dihydro-3H-indol-3-ylidine)-acetyl]-Glycyl-Leucyl-{(R)-2-Amino-5-phenylpentanoyl}-Arginyl-OH;

N-[(1,2-Dihydro-3H-indol-3-ylidine)-acetyl]-Glycyl-Leucyl-{(R)-2-Amino-5-phenylpentanoyl}-Arginyl-OH;

H-{(2S)-2-Amino-3-cyclohexylpropanoyl}(N-3-phenylpropyl)-Glycyl-Leucyl{(R)-2-Amino-5-phenylpentanoyl}-Arginyl-OH;

H-{(2S)-2-Amino-3-cyclohexylpropanoyl}(N-2-phenethyl)-Glycyl-Leucyl-{(R)-2-Amino-5-phenylpentanoyl}-Arginyl-OH;

N-[(Indol-3-yl)ethyl]-Glycyl-Leucyl{(R)-2-Amino-5-phenylpentanoyl}-Arginyl-OH;

N-[(Indoline-3-yl)acetyl]-Glycyl-Leucyl-{(R)-2-Amino-5-phenylpentanoyl}-Arginyl-OH;

H-Cysteinyl(S-benzyl)-Glycyl-Leucyl-{(R)-2-Amino-5-phenylpentanoyl}-Arginyl-OH;

H-Cysteinyl(S-1-phenethyl)-Glycyl-Leucyl-{(R)-2-Amino-5-Phenyl-pentanoyl}-Arginyl-OH;

N-(3-Phenylpropanoyl)-Glycyl-Leucyl-{(R)-2-Amino-5-phenylpentanoyl}-Arginyl-OH;

N-Phenylacetyl-Glycyl-Leucyl-{(R)-2-Amino-5-phenylpentanoyl}-Arginyl-OH;

H-{(R/S)-2-Amino-5-phenylpentanoyl}-Glycyl-Leucyl-{(R)-2-Amino-5-phenylpentanoyl}-Arginyl-OH;

N-(2-Aminocinnamoyl)-Glycyl-Leucyl-{(R)-2-Amino-5-phenylpentanoyl}-Arginyl-OH;

N-(2-Nitrocinnamoyl)-Glycyl-Leucyl-{(R)-2-Amino-5-phenylpentanoyl}-Arginyl-OH;

H-Phenylalanyl-Glycyl-Leucyl-{(R)-2-Amino-5-phenylpentanoyl}-Arginyl-OH;

H-{(S)-2-Amino-4-phenylbutyryl}-Glycyl-Leucyl-{(R)-2-Amino-5-phenyl-pentanoyl}-Arginyl-OH;

N-[(Indol-2-yl)-carbonyl]-Glycyl-Leucyl-{(R)-2-Amino-5-phenylpentanoyl}-Arginyl-OH; and N-(3-Cyclohexyl-2-hydroxypropionyl)-Glycyl-Leucyl-{(R)-2-Amino-5-phenylpentanoyl}-Arginyl-OH.

As used throughout this specification and the appended claims, the following terms have the meanings specified.

"Alkyl" refers to monovalent straight- or branched-chain groups of the specified number of carbon atoms, including, but not limited to methyl, ethyl, n-propyl, isopropyl, n-butyl, sec-butyl, isobutyl, tert-butyl, 2-methylhexyl, n-pentyl, 1-methylbutyl, 2,2-dimethylbutyl, 2-methylpentyl, 2,2-dimethylpropyl, n-hexyl, and the like.

"Amino" refers to a group having the structure —$NR^{22}R^{23}$, wherein $R^{22}$ and $R^{23}$ are independently selected from hydrogen, $C_1$–$C_8$-alkyl and aryl-$C_1$–$C_8$-alkyl, or $R^{22}$ and $R^{23}$ taken together is —$(CH_2)_{mm}$—, wherein mm is an integer of from 2-to-6. Amino includes, but is not limited to $H_2N$—, methylamino, dimethylamino, benzylamino, piperidinyl, N-benzyl-N-(3-phenylpropyl)amino, N-(2-phenylethyl)-N-(3-phenylpropyl)amino, N-(4-phenylbutyl)-N-(3-phenylpropyl)amino, and the like.

"Amino-$C_1$–$C_8$-alkyl" refers to, but is not limited to, aminomethyl, 2-aminoethyl, 3-aminopropyl, benzylaminomethyl, N-(2-phenylethyl)amino-ethyl, N-benzyl-N-methylaminomethyl, N-(2-phenylethyl)-N-ethylamino-ethyl, and the like.

"Amido-$C_1$–$C_8$-alkyl" refers to a group having the structure —NH—$C(O)R^{24}$, appended to an alkyl group, wherein $R^4$ is selected from hydrogen, $C_1$–$C_8$-alkyl, aryl and aryl-$C_1$–$C_8$-alkyl. "Anaphylatoxin" means C5a, C4a, C3a or the corresponding des-Arg degradation products.

The term "aryl", as used herein, refers to unsubstituted or mono- or di-substituted or phenyl or 1- or 2-naphthyl, wherein the 1- or 2-substituents are independently-selected from amino, halo, nitro, carboxy, cyano, $C_1$-to-$C_4$-alkyl, $C_1$–$C_8$-alkoxy, hydroxy, sulfonamido, trifluoromethyl and halo-mono-substituted $C_1$–$C_8$-alkyl.

The term "aryl-$C_1$–$C_8$-alkyl", as used herein, refers to an aryl group, as previously defined, appended to an alkyl group, including, but not limited to benzyl, 1- and 2-naphthylmethyl, halobenzyl, alkoxybenzyl, hydroxybenzyl, aminobenzyl, nitrobenzyl, guanidinobenzyl, phenylmethyl(benzyl), 1-phenylethyl, 2-phenylethyl, 1-naphthylethyl, and the like.

"(Carboxyamido)-$C_1$–$C_8$-alkyl" refers to a group of the formula, —$C(O)NR^{25}R^{26}$, appended to an alkyl group, wherein $R^{25}$ and $R^{26}$ are independently selected from hydrogen, $C_1$–$C_8$-alkyl, aryl and aryl-$C_1$–$C_8$-alkyl, or $R^{25}$ and $R^{26}$ taken together is —$(CH_2)_{pp}$— where pp is an integer of from 2-to-6.

"Cyclo-$C_3$–$C_6$-alkyl" refers to unsubstituted or mono- or di-substituted cyclic groups, of 3-to-6 carbons, including, but not limited to cyclopropyl, cyclobutyl, cyclopentyl, cyclohexyl and the like, wherein the 1 or 2 substituents are independently-selected from amino, aryl, nitro, carboxy, cyano, $C_1$-to-$C_8$ alkyl, $C_3$–$C_8$-alkoxy, guanidino, sulfonamido and trifluoromethyl.

"(Cyclo-$C_3$–$C_6$-alkyl)-$C_1$–$C_8$-alkyl" refers to, but is not limited to cyclopropylmethyl, cyclobutylmethyl, cyclopentylmethyl, cyclohexylmethyl, cycloheptylmethyl and cyclohexylethyl.

"Guanidino-$C_1$–$C_8$-alkyl" refers to a group of the structure —$NHC(=NH)NHR^{27}$, appended to an alkyl group, wherein $R^{27}$ is hydrogen, $C_1$–$C_8$-alkyl or aryl.

The term "Heterocyclic", as used herein, except where otherwise specified, refers to an unsubstituted or mono- or di-substituted 5- or 6-membered monocyclic ring containing carbon atoms and from one-to-three heteroatoms independently-selected from the group consisting of one nitrogen, one oxygen, or one sulfur; one oxygen and one nitrogen; one sulfur and one nitrogen; and one, two or three nitrogen, wherein the 5-membered ring has 0-to-2 double bonds and the 6-membered ring has 0-to-3 double bonds, wherein the nitrogen and sulfur heteroatoms may optionally be oxidized, and wherein the nitrogen heteroatom may optionally be quaternized or N-protected, or a bicyclic group in which any of the above monocyclic rings is fused to a benzene ring. Representative heterocycles include, but are not limited to pyrrolyl, pyrrolidinyl, pyrazolyl, pyrazolinyl, pyrazolidinyl, imidazolyl, imidazolinyl, imidazolidinyl, indolyl, pyridyl, piperidinyl, pyrazinyl, piperazinyl, pyrimidinyl, pyridazinyl, oxazoyl, oxazolidinyl, quinolyl, isoquinolyl, benzofuryl, benzothienyl, isoxazolyl, isoxazolidinyl, morpholinyl, thiazolyl, thiazolidinyl, isothiazolyl, isothiazolidinyl, benzimidazolyl, benzothiazolyl, benzoxazolyl, furyl and thienyl. The 1 or 2 substituents are independently-selected from amino, halo, hydroxy, nitro, carboxy, cyano, $C_1$-to-$C_8$-alkyl, $C_1$-to-$C_8$-alkoxy and sulfonamido.

"Naturally-occuring amino acid" refers to an amino acid selected from the group consisting of alanine, arginine, asparagine, aspartic acid, cysteine, glutamine, glutamic acid, glycine, histidine, isoleucine, leucine, lysine, methionine, ornithine, phenylalanine, proline, serine, threonine, tryptophan, tyrosine and valine.

"N-Terminal protecting group" or "N-protected" refers to those groups intended to protect the N-terminus or an amino group against undesirable reactions during synthetic procedures or to prevent the attack of exopeptidases on the final compounds or to increase the solubility of the final compounds and includes, but is not limited to acyl, acetyl, pivaloyl, tert-butylacetyl, tert-butyloxycarbonyl (Boc), carbobenzyloxy-carbonyl (Cbz), benzoyl groups or an L- or D-aminoacyl residue, which may itself be N-protected similarly. Other useful protecting groups may be found in Volume 3 of The Peptides, Gross, E. and Meienhofer, J., Academic Press, 1981 and Greene, T. W. and Wuts, P. G. M., *Protective Groups in Organic Synthesis*, 2nd Ed., John Wiley & Sons, 1991.

"Sulfhydryl-$C_1$–$C_8$-alkyl" refers to an —SH group appended to an alkyl group.

"Sulfonamido" refers to the group —$S(O)_2NH_2$.

"Thio-$C_1$–$C_8$-alkoxy" refers to an alkyl group attached to the parent molecule through a sulfur atom, exemplified by thiomethoxy, thioethoxy, thioisopropoxy, n-thiobutoxy, sec-thiobutoxy, isothiobutoxy, tert-thiobutoxy, and the like.

"(Thio-$C_1$–$C_8$-alkoxy)-$C_1$–$C_8$-alkyl" refers to a thioalkoxyl group appended to an alkyl group, and includes, but is not limited to, thiomethoxymethyl, thiomethoxyethyl, thioethoxymethyl and the like.

"Pharmaceutically-acceptable salt" means those salts, well known in the art, which are, within the scope of sound medical judgement, suitable for use in contact with the tissues of humans and lower animals without undue toxicity, irritation, allergic response and the like, and are commensurate with a reasonable benefit/risk ratio. For example, S. M Berge et al. describe pharmaceutically-acceptable salts in detail in *J. Pharmaceutical Sciences*, 1977, 66:1–19. The salts may be prepared in situ during the final isolation and purification of the compounds of formula (I), or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, iactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Examples of pharmaceutically-acceptable, non-toxic esters of the compounds of this invention include $C_1$-to-$C_6$ alkyl esters and cyclo-$C_5$-to-$C_7$-alkyl esters, as well as arylalkyl esters such as, but not limited to, benzyl. $C_1$-to-$C_4$ alkyl esters are preferred. Esters of the compound of formula A-B-D-E-G-J-L-M-N($R^4$)Arg-OH may be prepared according to conventional methods.

Examples of pharmaceutically-acceptable, non-toxic amides of the compounds of this invention include amides derived from ammonia, primary $C_1$-to-$C_6$-alkyl amines and secondary di-$C_1$-to-$C_6$-alkyl amines wherein the alkyl groups are straight or branched chain. In the case of secondary amines the amine may also be in the form of a 5- or 6-membered heterocycle containing one nitrogen atom. Amides derived from ammonia, $C_1$-to $C_3$-alkyl primary amides and di-$C_1$-to-$C_2$-alkyl secondary amides are preferred. Amides of the compound of formula A-B-D-E-G-J-L-M-N($R^4$)Arg-OH may be prepared according to conventional methods.

Numerous asymmetric centers may exist in the compounds of the present invention. The present invention contemplates the various stereoisomers and mixtures thereof. In particular, chiral centers can exist at >C($R^5$)($R^6$) , >C($R^7$)($R^8$), >C($R^9$)($R^{10}$), >C($R^{11}$)($R^{12}$), >C($R^{13}$)($R^{14}$), C($R^{15}$)($R^{16}$), and >C($R^{17}$)($R^{18}$).

Particular stereoisomers are prepared by selecting the starting amino acids or amino acid analogs having the desired stereochemistry and reacting these starting materials by the methods detailed below. Starting compounds of particular stereochemistry are either commercially available or are made by the methods detailed below and resolved by techniques well known in the organic chemical arts.

Method of Treatment

The compounds of the present invention serve to modulate the activity of anaphylatoxin, either as anaphylatoxin antagonists or as agonists. The antagonist compounds of the present invention block the anaphylatoxin receptor and prevent anaphylatoxin activity, which makes those compounds useful in the treatment and prevention of injurious conditions or diseases in which anaphylatoxin may be involved. Disease states or conditions in which anaphylatoxin has been implicated include asthma, bronchial allergy, chronic inflammation, systemic lupus erythematosus, vasculitis, serum sickness, angioedema, rheumatoid arthritis, osteoarthritis, gout, bullous skin diseases, hypersensitivity pneumonitis, idiopathic pulmonary fibrosis, immune complex-mediated glomerulonephritis, psoriasis, allergic rhinitis, adult respiratory distress syndrome, acute pulmonary disorders, endotoxin shock, hepatic cirrhosis, pancreatitis, inflammatory bowel diseases (including Crohn's disease and ulcerative colitis), thermal injury, Gram-negative sapsis, necrosis in myocardial infarction, leukophoresis, inflammatory response due to exposure to medical devices (including but not limited to hemodialyzer membranes and extracorpeal blood circulation equipment), chronic hepatitis, transplant rejection, post-viral encephalopathies, and/or ischemia induced myocardial or brain injury. These compounds may also be used as prophylactics for such conditions as shock accompanying Dengue fever. In addition, a combination of antibiotic and anti-inflammatory agent such as corticosteroids (e.g., methylprednisolone) and one or more of the above-mentioned compounds may be employed.

Certain compounds of the invention are useful therapeutic agents because of their ability to mimic or promote anaphylatoxin activity and are therefore useful in stimulating the inflammatory response and immune response in mammals which are deficient in this regard. These agonist compounds may be used to assist the body in building its defense mechanism against invasion by infectious microorganisms or other stresses. Interaction by these agonists at the anaphylatoxin receptor makes them useful in treating conditions or diseases including, but not limited to cancers (such as lung carcinoma), immunodeficiency diseases, and severe infections.

In some cases this will involve preventing the underlying cause of the disease state and in other cases, while the underlying disease will not be affected, the compounds of this invention will have the benefit of ameliorating the symptoms or preventing the manifestations of the disease.

The compounds of the present invention may be administered orally, parenterally, by inhalation spray, rectally, or topically in dosage unit formulations containing conventional nontoxic pharmaceutically-acceptable carriers, adjuvants and vehicles, as desired.

The term "parenteral" includes subcutaneous, intravenous, intramuscular, intrasternal, intra-arterial injection or infusion techniques, without limitation. "Topically" encompasses administration rectally and by inhalation spray, as well as by the more common mutes of the skin and the mucous membranes of the mouth and nose.

Actual dosage levels of active ingredients in the pharmaceutical compositions of this invention may be varied so as to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.05 mg to about 100 mg, more typically from about 0.1 mg to about 20 mg, of active compound per kilogram of body weight per day are administered daily to a mammalian host. If desired, the effective daily dose may be divided into multiple doses for purposes of administration, e.g., two-to-four separate doses per day.

Formulation of Pharmaceutical Composition

Pharmaceutical compositions of this invention for parenteral injection comprise pharmaceutically-acceptable sterile aqueous or nonaqueous solutions, dispersions, Suspensions or emulsions, as well as sterile powders for reconstitution into sterile injectable solutions or dispersions just prior to use. Examples of suitable aqueous and nonaqueous caders, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If desired, and for more effective distribution, the compounds may be incorporated into slow release or targeted delivery systems, such as polymer matrices, liposomes, and microspheres.

The injectable formulations may be sterilized, for example, by filtration through a bacterial-retaining filter; or by incorporating sterilizing agents in the form of sterile solid compositions which can be dissolved or dispersed in sterile water or other sterile injectable medium just prior to use.

Solid dosage forms for oral administration include capsules, tablets, caplets, powders, and granules. In such solid dosage forms, the active compound is mixed with at least one inert, pharmaceutically-acceptable excipient or carrier, such as sodium citrate or dicalcium phosphate, and/or (a) fillers or extenders, such as starches, lactose, sucrose, glucose, mannitol, and silicic acid, (b) binders, such as, for example, carboxymethylcellulose, alignates, gelatin, polyvinylpyrrolidone, sucrose, and acacia, (c) humectants, such as glycerol, (d) disintegrating agents, such as agar-agar, calcium carbonate, potato or tapioca starch, alginic add, certain silicates, and sodium carbonate, (e) solution retarding agents, such as paraffin, (f) absorption accelerators, such as quaternary ammonium compounds, (g) wetting agents, such as, for example, cetyl alcohol and glycerol monostearate, h) absorbents, such as kaolin and bentonite clay, and (i) lubricants, such as talc, calcium stearate, magnesium stearate, solid polyethylene glycols, sodium lauryl sulfate, and mixtures thereof. In the case of capsules, tablets and caplets, the dosage form may also comprise buffering agents.

Solid compositions of a similar type may also be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metehydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically-acceptable carrier and any needed preservatives, buffers, or propellants which may be required. Opthalmic formulations, eye ointments, powders and solutions are also contemplated as being within the scope of this invention.

Anaphylatoxin Receptor Binding $K_i$ Determination

Specific inhibition of C5a binding activity of representative compounds of the present invention was measured using 0.03–1 nM $^{125}$I-C5a with 2.5–25 I. Lg/mL of purified PMNL membrane fragments isolated according to the method described by Borregaard, N.; Heiple, J. M.; Simons, E. R.; and Clark, R. A., *J. Cell. Biol* 1983, 97, 52–61. (A more detailed description of the procedure used for determining receptor binding in PMNL membranes is described in Kawai, et al., *J. Med. Chem.*, 1991, 34, 2068–2071, at p. 2071.) In the assay, increasing concentrations of test compound were incubated with the PMNL membrane fragments and $^{125}$I-radiolabeled C5a for sixty minutes at ambient temperature. The membrane-bound radiolabeled C5a was separated from the free radiolabeled C5a by filtration, and the recovered gamma radioactivity was measured. The inhibition dissociation constant (apparent $K_i$) was calculated from the compound $IC_{50}$ values, estimated by linear regression analysis of the concentration-response data, using the method of Chang and Prusoff (*Biochem. Pharmacolo.* 1980, 69, 473–478). Free and membrane-bound ligand were separated by filtration. Binding potencies for representative examples of compounds of this invention are listed in Table 1. The in vitro binding at the C5a receptor is expected to result in in vivo modulation of C5a activity, as discussed in the Background of the Invention, above.

TABLE 1

In vitro C5a Receptor Binding Potency of Compounds of this Invention.

| Example | $K_i$ μM | Example | $K_i$ μM |
|---|---|---|---|
| 2 | 0.0048 | 3 | 0.013 |
| 8 | 0.66 | 9 | 0.11 |
| 10 | 0.23 | 11 | 3.6 |
| 12 | 17.8 | 13 | 21.1 |
| 14 | 1.38 | 15 | 0.046 |
| 16 | 0.23 | 17 | 0.025 |
| 18 | 19.6 | 19 | 3.04 |
| 20 | 6.65 | 21 | 1.1 |
| 22 | 4.7 | 25 | 4.5 |
| 26 | 0.4 | 27 | 0.45 |
| 28 | 1.72 | 30 | 7.1 |
| 31 | 1.1 | 32 | 10 |
| 33 | 0.68 | 34 | 21.6 |
| 35 | 1.27 | 36 | 9.7 |
| 37 | 3.2 | 38 | 8.4 |
| 39 | 71 | 40 | 1.1 |
| 41 | 25.4 | 42 | 0.45 |
| 43 | 136 | 43 | 7.9 |
| 45 | 7.58 | 46 | 22 |
| 47 | 1.1 | 48 | 0.23 |
| 49 | 0.72 | 50 | 0.19 |
| 51 | 0.14 | 52 | 10.3 |
| 53 | 0.1 | 54 | 0.46 |
| 55 | 7.7 | 56 | 26.78 |
| 57 | 1.93 | 58 | 6.5 |
| 59 | 67 | 60 | 19 |
| 61 | 3.2 | 62 | 1.07 |
| 63 | 0.4 | 64 | 0.47 |
| 65 | 0.30 | 66 | 0.046 |
| 67 | 5.26 | 68 | 14 |
| 69 | 0.14 | 70 | 4.5 |
| 71 | 0.15 | 72 | 4.27 |
| 73 | 1.99 | 74 | 91.9 |
| 75 | 17.2 | 76 | 1.5 |
| 77 | 0.05 | 78 | 0.07 |
| 79 | 0.39 | 80 | 0.87 |
| 81 | 0.11 | 83 | 0.42 |
| 84 | 3.9 | 85 | 2.0 |
| 86 | 44.8 | 87 | 5.8 |
| 88 | 26.5 | 89 | 6.4 |
| 90 | 0.18 | 91 | 0.39 |
| 92 | 0.75 | 93 | 0.17 |
| 94 | 5.8 | 95 | 34 |
| 96 | 33.2 | 97 | 8.2 |
| 98 | 44.7 | 99 | 4.8 |
| 100 | 60 | 101 | 52 |
| 102 | 21.7 | 103 | 1.32 |
| 104 | 2.4 | 105 | 0.33 |
| 106 | 0.41 | 107 | 0.087 |
| 108 | 4.8 | 109 | 4.8 |
| 110 | 9.3 | 111 | 1.0 |
| 112 | 17.8 | 113 | 0.87 |
| 114 | 18.6 | 115 | 5.6 |
| 116 | 0.63 | 117 | 0.37 |
| 118 | 3.7 | 119 | 13 |
| 120 | 0.34 | 121 | 7.15 |
| 122 | 2.5 | 123 | 0.065 |
| 124 | 34 | 125 | 0.83 |
| 126 | 13.4 | 127 | 23.3 |
| 128 | 0.027 | 129 | 0.017 |
| 130 | 0.14 | 131 | 0.56 |
| 132 | 0.42 | 133 | 27.9 |
| 134 | 1.76 | 135 | 1.3 |
| 136 | 7.2 | 137 | 4.2 |
| 138 | 0.33 | 139 | 1.1 |
| 140 | 18.6 | 141 | 16 |
| 142 | 1.3 | 143 | 0.054 |
| 144 | 5.27 | 145 | 7 |

Synthesis of the Compounds

The novel compounds and salts thereof of the invention can be utilized effectively as therapeutic agents. Accordingly, the present invention further relates to therapeutic compositions comprising a novel compound having the general formula (I), or salts thereof, as an active component.

The compounds of the invention may be prepared by a synthetic method of elongation of a peptide chain through condensation of one amino acid by one, or by a method of coupling fragments consisting of two or several amino acids, or by a combination of these methods in accordance with conventional peptide synthesis methods.

The condensation of two amino acids, the condensation of an amino acid with a peptide or the condensation of one peptide with another peptide may be effected in accordance with conventional condensation methods such as azide method, mixed acid anhydride method, symmetrical anhydride method, DCC (dicyclohexylcarbodiimide) method, active ester method (p-nitrophenyl ester method, N-hydroxysuccinimide ester method, cyanomethyl ester method and the like), Woodward reagent K method, the dicyclohexylcarbodiimide/1-hydroxy-benzotriazole (DCC-HOBT) method and the like. These condensation reactions may be done by either solution methods or solid phase synthetic methods. When the peptide chain is elongated by the solid phase method, the C-terminal amino acid is linked to an insoluble carrier. As the insoluble carrier, any that can produce a detachable bond by reacting with a carboxyl group in a C-terminal amino acid may be used, and the examples thereof involve, for example, halomethyl resins such as chloromethyl resin, bromomethyl resin and the like and hydroxymethyl resin.

As conventional polypeptide synthesis, branched chain amino and carboxyl groups at alpha and omega positions in amino acids may be protected/deprotected if necessary. The protecting groups for amino groups which may be used involve, for example, benzyloxycarbonyl (Z), o-chlorobenzyloxycarbonyl ((2-CI)Z), p-nitrobenzyloxycarbonyl (Z(NO$_2$)), p-methoxybenzyloxycarbonyl (Z(OMe)), t-butoxycarbonyl (Boc), t-amyloxycarbonyl (Aoc), isobornyloxycarbonyl, admantyloxycarbonyl, 2-(4-biphenyl)-2-propyloxycarbonyl (Bpoc), 9-fluorenyl-methoxycarbonyl (Fmoc), methylsulfonylethoxycarbonyl (Msc), trifluoroacetyl, phthalyl, formyl, 2-nitrophenylsulfenyl (Nps), diphenylphosphinothioyl (Ppt), and dimethylphosphinothioyl (Mpt), as discussed under the definition of "N-terminal protecting groups", above.

The examples of protecting groups for carboxyl groups involve, for example, benzyl ester (OBn), cyclohexyl ester, 4-nitrobenzyl ester (OBnNO$_2$), t-butyl ester (OtBu), 4-picolyl ester (OPic) and the like.

In the course of the synthesis of the present novel compounds, specific amino acids having functional groups other than amino and carboxyl groups in the branched chain such as arginine, cysteine, serine, and the like may be protected, if necessary, with suitable protecting group. It is preferable that for example, the guanidino group (N$^G$) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzene-sulfonyl (Mds), 1,3,5-trimethylphenylsulfonyl (Mts) and the like, and the thiol group in cysteine may be protected with benzyl, p-methoxybenzyl, triphenylmethyl, acetamidomethyl, ethylcarbamyl, 4-methylbenzyl (4-MeBn), 2,4,6-trimethylbenzyl (Tmb) and the like, and the hydroxyl group in serine may be protected with benzyl (Bn), t-butyl, acetyl, tetrahydropyranyl, and the like.

The following literature procedures were used to prepare N-alkyl-or N,N-dialkyl-amino acid derivatives: Lovett, J. A. and portoghese, P., *J. Med. Chem.* 1987, 30, 1144–1149; Borch, R. F. and Hassid, A. I., *J. Org. Chem.* 1972, 37, 1673–1674; Hansen, D. W. and Pilipauskas, D., *J. Org. Chem.* 1985, 50, 945–950; Grieco, P. A. and Basha, A., *J. Org. Chem.* 1987, 52, 5746–5749; Shuman, R. T.; Smithwick, E. L.; Smiley, D. L.; Brooke, G. S. and Gesellchen, P. D., "Peptide: Structure and Function", Proceedings of the Eighth American Peptide Symposium, 1984; p 143–146; Cheung, S. T. and Benoiton, N. L., Can. J. Chem. 1977, 55, 906–910. These reactions were carried out either on the elongated peptide-resin or on amino acid derivatives and then incorporated into the peptide-resin.

(N-Boc)-(2R)-2-Amino-3-cyclohexylpropanoic acid: A solution of Boc-D-phenylalanine (50 g, 0.19 mol) in methanol (500 mL) was hydrogenated at ambient temperature at 4 atmospheres with 5% rhodium on alumina (5.0 g). Removal of catalyst by filtration and evaporation yielded the product quanititatively. The (2S)-isomer was prepared in an identical manner from Boc-L-phenylalanine.

The compounds of the invention were prepared by standard solid phase peptide synthesis conditions as described in *Solid Phase Peptide Synthesis* by J. M. Stewart and J. D. Young, Second Edition (1984) and illustrated in Examples 1 and 2 in the experimental section.

The compounds of the invention may also be prepared by partial solid phase synthesis, fragment condensation methods and classical solution methods as exemplified by the methods described in *Peptide Synthesis*, Second Edition, M. Bodanszky, Y. S. Klausner; and M. A. Ondetti (1976).

The standard chirality descriptors "R" and "S" are used to indicate an isomerically pure center, "RS" to indicate a mixture, and "R/S" to indicate a single pure isomer of undetermined configuration. The descriptor "±" refers to a d,l mixture of amino acids at the indicated residue. The descriptor ψ{X} indicates the group, X, that is a replacement for the standard peptide bond, —C(O)NH—.

The foregoing may be better understood by reference to the following examples which are provided for illustration and not limitation of the practice of the invention. Unless otherwise indicated, the standard peptide methods described above and in Examples 1 and 2 are used to assemble the different products, using the precursors indicated by the specific peptide sequence. The synthetic products were at least 95% pure, and gave NMR and mass spectra consistent with the proposed structure.

EXAMPLE 1

H-Phenylalanyl-Lysyl(N-epsilon-Cbz)-Prolyl-{(2S)-2-Amino-3-cyclohexylpropanoyl}-Alanyl-Leucyl-{(R)-2-Amino-5-phenylpentanoyl}-Arginyl(N-guanidino-Tos)-Merrifield Resin Boc-L-Arg(N-guanidino-Tos)-Merrifield resin (0.4–1.0 g) was placed in a solid phase peptide synthesis vessel and amino acids were attached to the resin sequentially in the following order: Boc-(R)-2-Amino-5-phenylpentanoic Acid, Boc-Leucine, Boc-L-Alanine, Boc-(2S)-2-Amino-3-cyclohexylpropanoic Acid, Boc-Proline, N-alpha-Boc-Lysine(N-epsilon-Cbz), Boc-Phenylalanine, according to the protocol outlined in Agenda A to yield the protected peptide resin: H-Phenylalanyl-Lysyl(N-epsilon-Cbz)-Prolyl-{(2S)-2-Amino-3-cyclohexylpropanoyl}-Alanyl-Leucyl-{(R)-2-Amino-5-phenylpentanoyl}-Arginyl(N-guanidino-Tos)-Merrifield Resin.

Following the synthesis, the protected peptide resin was removed from the reaction vessel by washing the resin three times with 20 mL DMF into a 30–60 mL sintered glass funnel, followed by washing the resin three times with 20 mL methylene chloride. The resin was added at least five hours, then weighed.

Agenda A

1. Deblock: 45% trifluoroacetic acid (TFA) in methylene chloride containing 2.5% anisole (v/v/v).
2. Neutralization: 10% diisopropylethylamine (DIEA) in methylene chloride (v/v).
3. Single Coupling: 0.2–0.4M Boc-amino acid derivative in N,N-dimethylformamide (DMF), 0.2–0.4M diisopropylcarbodiimide (DIC) in methylene chloride, reaction time, 60 minutes.
4. Resin base washing: 10% DIEA in methylene chloride (v/v).
5. Single Coupling repeated: same as Step 3.
6. Go to next amino acid residue (go back to Step 1).
7. Upon attachment of the final amino acid to the growing peptide chain, the protecting group (t-Boc) is removed as in Step 1.

EXAMPLE 2

H-Phenylalanyl-Lysyl-Prolyl-{(2S)-2-Amino-3-cyclohexylpropanoyl}-Alanyl-Leucyl-{(R)-2-Amino-5-phenylpentanoyl}-Arginyl-OH The protected peptide resin of Example 1 (600 mg) was treated with 1.0 mL of anisole and 10 mL of hydrogen fluoride (HF) for 60 minutes at 0° C. The HF and anisole were removed in vacuo at 0° C., and the mixture of the pepetide and resin was washed with diethyl ether (2×25 mL). The crude pepetide was extracted from the mixture by treatment with portions of 20% aqueous acetic acid (4×25 mL), lyophilized to a dry amorphous powder, and purified by high performance liquid chromatography (HPLC) (column 21.4 mm ID×25 cm or 41.4 mm ID×25 cm, Dynamax (Rainin), 8 μm silica, C18 reverse-phase column). The sample was purified by gradient elution {from 20 to 60% (80% acetonitrile in water with 0.1% trifluoroacetic acid)} at a flow rate of 15–45 mL/minute. MS (FAB) m/e 1059 (M+H)$^+$. Amino Acid Analysis: Phe (0.97), Lys (0.99), Pro (1.02), Cha (1.00), Ala (0.97), Leu (1.04), Arg (1.00).

EXAMPLE 3

H-Phenylalanyl-Lysyl-Prolyl-{(2S)-2-Amino-3-cyclohexylpropanoyl}-Alanyl-Leucyl-{(S)-2-Amino-5-phenylpentanoyl}-Arginyl-OH This compound was prepared in analogy to Example 2 using the corresponding {(S)-2-Amino-5-phenylpentanoyl} resin. MS (FAB) m/e 1059 (M+H)$^+$. Amino Acid Analysis: Phe (0.95), Lys (1.00), Pro (1.00), Cha (1.00), Ala (0.97), Leu (1.04), Arg (1.00).

EXAMPLE 4

2-(R)-Amino-5-phenylpentanoic acid (±)-2-Amino-5-phenylpentanoic acid (35 g) was suspended in water (3 L) and solubilized by adjusting the pH to 12 with 7N sodium hydroxide solution. The pH was readjusted to pH 8 using 1M phosphoric acid with continuous stirring at 45° C. The solution was allowed to cool to 40° C. and L-amino acid oxidase (Sigma, 0.7 unit/mg) was added.

The reaction was stirred with good aeration at 37°–40° C. for two weeks. The reaction was monitored using the following High Pressure Liquid Chromatography (HPLC) system: C-18 Waters analytical column, 20% acetonitrile in Buffer (0.624 g/L $CuSO_4.5H_2O$, 0.576 g/L L-proline, 2 g/L ammonium acetate, and 1L of water with the pH of the solution adjusted to pH 7 with ammonium hydroxide); 2 mL/minute flow rate; fluorescence detection: Ex 345 nm, Em>415 nm; OPA derivatization: 300 μL of 1N sodium borate pH 9.4, 50 mL of 20 mg ortho-phthalaldehyde (OPA) plus 24 ng N-acetyl cysteine/6 mL 50% methanol/water; incubate 3 minutes at ambient temperature. When the digestion of the L-enantiomer was complete, the reaction mixture was concentrated to 500 mL by removing water in vacuo. The pH was adjusted to 5 and the predpitate was collected by filtration and recrystallization from ethanol-water to afford 17.32 g (99%) of the title compound.

EXAMPLE 5

(±)-2-Amino-5-phenylpentanoic acid

Diethyl acetamidomalonate (220 g) in 1 L of absolute ethanol was added to a stirred solution of sodium ethoxide in ethanol, prepared by dissolving sodium (24 g) in absolute ethanol (500 mL), under nitrogen. The reaction mixture was refluxed under nitrogen for 30 minutes and then 1-bromo-3-phenylpropane (200 g) was added. The reaction mixture was refluxed overnight, cooled to ambient temperature, the precipitate removed by filtration and the solvent removed in vacuo. Concentrated hydrochloric acid (800 mL) was added to the residue and the reaction mixture was refluxed for 14 hours. The cooled aqueous solution was washed with ether (2×200 mL). The residual ether in the aqueous phase was removed by nitrogen bubbling through the solution. The pH of the aqueous phase was adjusted to 7–8 by the addition of ammonium hydroxide. The title compound was collected by filtration, air dried and recrystallized from ethanol-water to afford 150 g (83%). m.p. 255°–257° C. MS (FAB) m/e 194 $(M+H)^+$.

EXAMPLE 6

Boc-2-(R)-Amino-5-phenylpentanoic add

Di-tert-butyl dicarbonate (15 g) in 50 mL of tert-butanol was added dropwise to a stirred solution of 2-(R)-amino-5-phenylpentanoic acid (9 g) dissolved in 50 mL of 1N sodium hydroxide solution. The solution was stirred at ambient temperature overnight and then washed with hexanes (2×100 mL). The aqueous phase was adjusted to pH 2 with 1N hydrochloric acid and extracted with ethyl ether (3×100 mL). The combined organic extracts were washed once with saturated brine (100 mL), dried over magnesium sulfate and concentrated in vacuo to afford 12 g (88%) of the title compound as a white solid. MS (FAB) m/e 294 $(M+H)^+$.

EXAMPLE 7

Boc-(±)-2-Amino-5-phenylpentanoic acid

Di-tert-butyl dicarbonate (24 g) in 100 mL of tert-butanol was added dropwise to a stirred solution of (+)-2-amino-5-phenylpentanoic acid (21 g) dissolved in 150 mL of 1N sodium hydroxide solution. The solution was stirred at ambient temperature overnight and then washed with hexanes (2×100 mL). The aqueous phase was adjusted to pH 2 with 1N hydrochloric acid and extracted with ethyl ether (3×100 mL). The combined organic extracts were washed once with saturated brine (100 mL), dried over magnesium sulfate and concentrated in vacuo to afford 30 g (88%) of the title compound as a white solid. MS (FAB) m/e 294 $(M+H)^+$.

The compounds of Examples 8–146 were prepared using generally known methods of peptide synthesis as exemplified in Examples 1–2.

EXAMPLE 8

H-Phenylalanyl-Lysyl-Alanyl-{(2S)-2-Amino-3-cyclohexylpropanoyl}-Alanyl-DPhenylalanyl-{(R/S)-2-Amino-5-phenylpentanoyl}-Arginyl-OH MS (FAB) m/e 1067 $(M+H)^+$. Amino Acid Analysis: Phe (1.96), Lys (0.96), Ala (2.03), Cha (0.99), Arg (1.06).

EXAMPLE 9

H-Phenylalanyl-Lysyl-Alanyl-{(2S)-2-Amino-3-cyclohexylpropanoyl}-Alanyl-DPhenylalanyl-{(R/S)-2-Amino-5-phenylpentanoyl}-Arginyl-OH MS (FAB) m/e 1067 $(M+H)^+$. Amino Acid Analysis: Phe (1.97), Lys (0.95), Ala (2.02), Cha (0.99), Arg (1.06).

EXAMPLE 10

H-Lysyl-Glycyl-{(2S)-2-Amino-3-cyclohexylpropanoyl}-Glycyl-Leucyl-{(R/S)-2-Amino-5-phenylpentanoyl}-Arginyl-OH MS (FAB) m/e 858 $(M+H)^+$. Amino Acid Analysis: Lys (1.02), Gly (1.88), Cha (0.96), Leu (1.10), Arg (1.00).

EXAMPLE 11

N-(6-Aminohexanoyl)-{(2S)-2Amino-3-cyclohexylpropanoyl}-Prolyl-Leucyl-{(R/S)-2-Amino-5-phenylpentanoyl}-Arginyl-OH MS (FAB) m/e 826 $(M+H)^+$. Amino Acid Analysis: Cha (1.02), Pro (1.02), Leu (1.04), Arg (0.94).

EXAMPLE 12

N-(6-Aminohexanoyl)-{(2S)-3-Amino-3-cyclohexylpropanoyl}-Prolyl-Leucyl-{(R/S)-2-Amino-5-phenylpentanoyl}-Arginyl-OH MS (FAB) m/e 826 $(M+H)^+$.

EXAMPLE 13

N-(6-Aminohexanoyl)-(N-methyl){(2S)-2-Amino-3-cyclohexylpropanoyl}-Glycyl-Leucyl-{(R/S)-2-Amino-5-phenylpentanoyl}-Arginyl-OH MS (FAB) m/e 800 $(M+H)^+$.

EXAMPLE 14

N-(6-Aminohexanoyl)-(N-methyl){(2S)-2-Amino-3-cyclohexylpropanoyl}-Glycyl-Leucyl-{(R/S)-2-Amino-5-phenylpentanoyl}-Arginyl-OH MS (FAB) m/e 800 $(M+H)^+$. Amino Acid Analysis: Gly (0.94), Leu (1.07), Arg (1.00).

EXAMPLE 15

N-(3-Phenylpropyl)-Tryptophanyl-Glycyl-Leucyl-{(R)-2-Amino-5-phenylpentanoyl}-Arginyl-OH MS (FAB) m/e 824 $(M+H)^+$.

EXAMPLE 16

H-Phenylalanyl-Lysyl-Alanyl-{(2S)-2-Amino-3-cyclohexylpropanoyl}-Alanyl-Phenylalanyl-{(R/S)-2-Amino-5-phenylpentanoyl}-Arginyl-OH MS (FAB) m/e 1067 (M+H)$^+$.

EXAMPLE 17

H-Phenylalanyl-Lysyl-Alanyl-{(2S)-2-Amino-3-cyclohexylpropanoyl}-Alanyl-Phenylalanyl-{(R/S)-2-Amino-5-phenylpentanoyl}-Arginyl-OH MS (FAB) m/e 1067 (M+H)$^+$. Amino Acid Analysis: Phe (1.97), Lys (0.97), Ala (2.02), Cha (0.99), Arg (1.05).

EXAMPLE 18

N-(4-Aminocyclohexanoyl)-{(2S)-2-Amino-3-cyclohexylpropanoyl}-Glycyl-Leucyl-{(R/S)-2-Amino-5-phenylpentanoyl}-Arginyl-OH MS (FAB) m/e 812 (M+H)$^+$.

EXAMPLE 19

N-(4-Aminocyclohexanoyl)-{(2S)-2-Amino-3-cyclohexylpropanoyl}-Glycyl-Leucyl-{(R/S)-2-Amino-5-phenylpentanoyl}-Arginyl-OH MS (FAB) m/e 812 (M+H)$^+$. Amino Acid Analysis: Cha (0.95), Gly (1.01), Leu (1.10), Arg (1.09).

EXAMPLE 20

N-{Indole-3-acetyl}-Leucyl-{(S)-2-Amino-5-phenylpentanoyl}-Arginyl-OH

MS (FAB) m/e 620 (M+H)$^+$.

EXAMPLE 21

H-Glycyl-Lysyl-Prolyl-{(2S)-2-Amino-3-cyclohexylpropanoyl}-Alanyl -Leucyl-DCysteinyl (S-phenethyl)-Arginyl-OH MS (FAB) m/e 1001 (M+H)$^+$. Amino Acid Analysis: Gly (1.00), Lys (0.94), Pro (1.00), Ala (1.00), Leu (1.00), Arg (1.00).

EXAMPLE 22

H-Glycyl-Lysyl-Prolyl-{(2S)-2-Amino-3-cyclohexylpropanoyl}-Alanyl-Leucyl-DCysteinyl(S-3-phenylpropyl)-Arginyl-OH MS (FAB) m/e 1015 (M+H)$^+$. Amino Acid Analysis: Gly (1.00), Lys (0.95), Pro (1.00), Cha (0.94), Ala (1.00), Leu (1.06), Arg (1.00).

EXAMPLE 23

N-{(2S)-2-Amino-3-cyclohexylpropanoyl}-Alanyl-Leucyl-{(R)-2-Amino-5-phenylpentanoyl}-Arginyl-OH MS (FAB) m/e 687 (M+H)$^+$. Amino Acid Analysis: Cha (0.91), Ala (0.97), Leu (1.02), Arg (1.02).

EXAMPLE 24

H-Prolyl-{(2S)-2-Amino-3-cyclohexylpropanoyl}-Alanyl-Leucyl-{(S)-2-Amino-5-phenylpentanoyl}-Arginyl-OH MS (FAB) m/e 784 (M+H)$^+$. Amino Acid Analysis: Pro (0.95), Cha (0.95), Ala (0.96), Leu (1.01), Arg (1.03).

EXAMPLE 25

N-(6-Aminohexanoyl)-Phenylalanyl(N-methyl)-Glycyl-Leucyl-{(R/S)-2-Amino-5-phenylpentanoyl}-Arginyl-OH MS (FAB) m/e 794 (M+H)$^+$.

EXAMPLE 26

N-(6-Aminohexanoyl)-Phenylalanyl(N-methyl)-Glycyl-Leucyl-{(R/S)-2-Amino-5-phenylpentanoyl}-Arginyl-OH MS (FAB) m/e 794 (M+H)$^+$. Amino Acid Analysis: NMePhe (1.06), Gly (0.93), Leu (1.08), Arg (0.99).

EXAMPLE 27

N-(7-Aminoheptanoyl)-{(2S)-2-Amino-3-cyclohexylpropanoyl}-Glycyl-Leucyl(N-methyl)-{(R/S)-2-Amino-5-phenylpentanoyl}-Arginyl-OH MS (FAB) m/e 814 (M+H)$^+$. Amino Acid Analysis: Cha (1.02), Gly (0.94), Phe (0.94), Arg (1.06).

EXAMPLE 28

N-(7-Aminoheptanoyl)-{(2S)-2-Amino-3-cyclohexylpropanoyl}-Glycyl-Leucyl-[{(R/S)-2-Amino-5-phenylpentanoyl} (N-methyl)-Arginyl-OH
MS (FAB) m/e 814 (M+H)$^+$.

EXAMPLE 29

N-(7-Aminoheptanoyl)-{(2S)-2-Amino-3-cyclohexylpropanoyl}-Glycyl-Leucyl-{(R/S)-2-Amino-5-phenylpentanoyl}(N-methyl)-Arginyl-OH MS (FAB) m/e 814 (M+H)$^+$. Amino Acid Analysis: Cha (0.91), Gly (1.04), Arg (1.01).

EXAMPLE 30

N-(Indole-3-butyryl)-Leucyl-{(R/S)-2-Amino-5-phenylpentanoyl}-Arginyl-OH

MS (FAB) m/e 648 (M+H)$^+$.

Example 31

H-Glycyl-Lysyl-Propyl-{(2S)-2-Amino-3-cyclohexylpropanoyl}-Alanyl-Leucyl-DCysteinyl(S-benzyl)-Arginyl-OH The cysteine residue of the corresponding cysteine containing pepetide was alkylated with benzyl bromide using the procedure described by Or, Y. S.; Clark, R. F.; Luly, J. R. J. Org. Chem. 1991, 56, 3146. MS (FAB) m/e 987 (M+H)$^+$. Amino Acid Analysis: Gly (0.98), Lys (1.01), Pro (0.99), Ala (0.99), Leu (1.04), Arg (0.99).

EXAMPLE 32

N-(6-Aminohexanoyl)-Glycyl-{(2S)-2-Amino-3-cyclohexylpropanoyl}-Alanyl-Leucyl-{(R/S)-2-Amino-5-phenylpentanoyl}-Arginyl-OH MS (FAB) m/e 857 (M+H)$^+$.

EXAMPLE 33

N-(6-Aminohexanoyl)-Glycyl-{(2S)-2-Amino-3-cyclohexylpropanoyl}-Alanyl-Leucyl-{(R/S)-2-Amino-5-phenylpentanoyl}-Arginyl-OH MS (FAB) m/e 857 (M+H)⁺. Amino Acid Analysis: Gly (0.89), Cha (0.93), Ala (1.02), Leu (1.08), Arg (1.10).

EXAMPLE 34

N-(6-Aminohexanoyl)-{(2R)-2-Amino-3-cyclohexylpropanoyl}-Glycyl-Leucyl-{(R/S)-2-Amino-5-phenylpentanoyl}-Arginyl-OH MS (FAB) m/e 786 (M+H)⁺.

EXAMPLE 35

N-(6-Aminohexanoyl)-{(2R)-2-Amino-3-cyclohexylpropanoyl}-Glycyl-Leucyl-{(R/S)-2-Amino-5-phenylpentanoyl}-Arginyl-OH MS (FAB) m/e 786 (M+H)⁺. Amino Acid Analysis: Cha (0.87), Gly (0.91), Leu (1.06), Arg (1.04).

EXAMPLE 36

N-(5-Aminopentanoyl)-{(2S)-2-Amino-3-cyclohexylpropanoyl}(N-methyl)-Glycyl-Leucyl-{(R/S)-2-Amino-5-phenylpentanoyl}-Arginyl-OH MS (FAB) m/e 786 (M+H)⁺.

EXAMPLE 37

N-(5-Aminopentanoyl)-{(2S)-2-Amino-3-cyclohexylpropanoyl}N-methyl)-Glycyl-Leucyl-{(R/S)-2-Amino-5-phenylpentanoyl}-Arginyl-OH MS (FAB) m/e 786 (M+H)⁺. Amino Acid Analysis: Gly (0.95), Leu (1.03), Arg (1.03).

EXAMPLE 38

N=(Indole-3-propionyl)-Leucyl-{(R)-2-Amino-5-phenylpentanoyl}-Arginyl-OH

MS (FAB) m/e 634 (M+H)⁺.

EXAMPLE 39

H-Lysyl-Aspartyl-Methionyl-Glutaminyl-Leucyl-{(R/S)-2-Amino-5-phenylpentanoyl}-Arginyl-OH MS (FAB) m/e 965 (M+H)⁺.

EXAMPLE 40

H-Lysyl-Aspartyl-Methionyl-Glutaminyl-Leucyl-{(R/S)-2-Amino-5-phenylpentanoyl}-Arginyl-OH MS (FAB) m/e 965 (M+H)⁺.

EXAMPLE 41

H-Lysyl-{( 2S)-2-Amino-3-cyclohexylpropanoyl}-Glycyl-Leucyl-{(R/S)-2-Amino-5-phenylpentanoyl}-Arginyl-OH MS (FAB) m/e 801 (M+H)⁺.

EXAMPLE 42

H-Lysyl-{( 2S)-2-Amino-3-cyclohexylpropanoyl}-Glycyl-Leucyl-{(R/S)-2-Amino-5-phenylpentanoyl}-Arginyl-OH MS (FAB) m/e 801 (M+H)⁺. Amino Acid Analysis: Lys (0.96), Cha (0.94), Gly (1.07), Leu (1.03), Arg (0.99).

EXAMPLE 43

N-(6-Aminohexanoyl)-{(2S)-2-Amino-3-cyclohexylpropanoyl}-Glycyl-Phenylalanyl-{(R/S)-2-Amino-5-phenylpentanoyl}-Arginyl-OH MS (FAB) m/e 820 (M+H)⁺.

EXAMPLE 44

N-(6-Aminohexanoyl)-{(2S)-2-Amino-3-cyclohexylpropanoyl}-Glycyl-Phenylalanyl-{(R/S)-2-Amino-5-phenylpentanoyl}-Arginyl-OH MS (FAB) m/e 820 (M+H)⁺. Amino Acid Analysis: Cha (1.00), Gly (0.91), Phe (1.05), Arg (1.04).

EXAMPLE 45

N-Acetyl-{(2S)-2-Amino-3-cyclohexylpropanoyl}-Glycyl-Leucyl-{(R/S)-2-Amino-5-phenylpentanoyl}-Arginyl-OH MS (FAB) m/e 715 (M+H)⁺. Amino Acid Analysis: Cha (1.07), Gly (0.90), Leu (0.96), Arg (1.07).

EXAMPLE 46

N-Acetyl-{( 2S)-2-Amino-3-cyclohexylpropanoyl}-Glycyl-Leucyl-{(R/S)-2-Amino-5-phenylpentanoyl}-Arginyl-OH MS (FAB) m/e 715 (M+H)⁺.

EXAMPLE 47

N-Phenylacetyl-{(2S)-2-Amino-3-cyclohexylpropanoyl}-Glycyl-Leucyl-{(R)-2-Amino-5-phenylpentanoyl}-Arginyl-OH MS (FAB) m/e 791 (M+H)⁺. Amino Acid Analysis: Cha (0.89), Gly (0.94), Leu (1.03), Arg (1.03).

EXAMPLE 48

N-(7-Aminoheptanoyl)-{(2S)-2-Amino-3-cyclohexylpropanoyl}-Glycyl-Leucyl-{(+)-2-Amino-3-phenoxybutyryl}-Arginyl-OH (±)-2-Amino-3-phenoxybutyric acid was prepared from diethyl acetamidomalonate and 2-phenoxyethyl chloride by the procedures described in Example 5 and 6. MS (FAB) m/e 802 (M+H)⁺. Amino Acid Analysis: Cha (0.95), Gly (0.94), Leu (1.03), Arg (1.03).

EXAMPLE 49

N-(3-Phenylpropanoyl)-{(2S)-2-Amino-3-cyclohexylpropanoyl}-Glycyl-Leucyl-{(R)-2-Amino-5-phenylpentanoyl}-Arginyl-OH MS (FAB) m/e 805 (M+H)⁺. Amino Acid Analysis: Cha (0.94), Gly (0.95), Leu (1.05), Arg (0.96).

EXAMPLE 50

N-(Indole-3-acetyl)-Glycyl-Leucyl-{(R)-2-Amino-5-phenylpentanoyl}-Arginyl-OH

MS (FAB) m/e 677 (M+H)⁺.

EXAMPLE 51

N-(4-Phenylbutyryl)-{(2S)-2-Amino-3-cyclohexylpropanoyl}-Glycyl-Leucyl-{(R)-2-Amino-5-phenylpentanoyl}-Arginyl-OH MS (FAB) m/e 805 (M+H)⁺. Amino Acid Analysis: Gly (0.93), Leu (1.03), Arg (1.03).

EXAMPLE 52

H-Glycyl-Lysyl-Prolyl-{(2S)-2-Amino-3-cyclohexylpropanoyl}-Alanyl-Leucyl-{(R/S)-2-Amino-5-phenylpentanoyl}-Arginyl-OH MS (FAB) m/e 969 (M+H)$^+$. Amino Acid Analysis: Gly (0.90), Lys (1.05), Pro (1.01), Cha (0.98), Ala (1.05), Leu (1.08), Arg (1.10).

EXAMPLE 53

H-Glycyl-Lysyl-Prolyl-{(2S)-2-Amino-3-cyclohexylpropanoyl}-Alanyl-Leucyl-{(R/S)-2-Amino-5-phenylpentanoyl}-Arginyl-OH MS (FAB) m/e 969 (M+H)$^+$. Amino Acid Analysis: Gly (1.00), Lys (1.07), Pro (1.00), Ala (1.00), Leu (1.00), Arg (0.95).

EXAMPLE 54

H-{(2S)-2-Amino-3-cyclohexylpropanoyl}-Glycyl-Leucyl-{(R/S)-2-Amino-5-phenylpentanoyl}-Arginyl-OH MS (FAB) m/e 673 (M+H)$^+$. Amino Acid Analysis: Cha (0.90), Gly (1.02), Leu (1.06), Arg (1.02).

EXAMPLE 55

H-{(2S)-2-Amino-3-cyclohexylpropanoyl}-Glycyl-Leucyl-{(R/S)-2-Amino-5-phenylpentanol}-Arginyl-OH MS (FAB) m/e 673 (M+H)$^+$.

EXAMPLE 56

H-DLysyl-{(2S)-2-Amino-3-cyclohexylpropanoyl}-Glycyl-Leucyl-{(R/S)-2-Amino-5-phenylpentanoyl}-Arginyl-OH MS (FAB) m/e 801 (M+H)$^+$.

EXAMPLE 57

H-DLysyl-{(2S)-2-Amino-3-cyclohexylpropanoyl}-Glycyl-Leucyl-{(R/S)-2-Amino-5-phenylpentanoyl}-Arginyl-OH MS (FAB) m/e 801 (M+H)$^+$. Amino Acid Analysis: Lys (0.96), Cha (0.92), Gly (1.09), Leu (1.04), Arg (0.99).

EXAMPLE 58

N-(6-Aminohexanoyl)-{(2S)-2-Amino-3-cyclohexylpropanoyl}-Glycyl-DPhenylalanyl-{(R/S)-2-Amino-5-phenylpentanoyl}-Arginyl-OH MS (FAB) m/e 820 (M+H)$^+$. Amino Acid Analysis: Cha (1.00), Gly (0.92), Phe (1.02), hhPhe (0.95), Arg (1.05).

EXAMPLE 59

H-{(2S)-2-Amino-3-cyclohexylpropanoyl}-Glycyl-Alanyl-{(±)-2-Amino-5-phenylpentanoyl}-Arginyl-OH MS (FAB) m/e 631 (M+H)$^+$. Amino Acid Analysis: Cha (1.02), Gly (0.82), Ala (0.99), hhPhe (1.05), Arg (1.10).

EXAMPLE 60

N-(7-Aminoheptanoyl)-{(2S)-2-Amino-3-cyclohexylpropanoyl}-Sarconsinyl-Leucyl-{(R/S)-2-Amino-5-phenylpentanoyl}-Arginyl-OH MS (FAB) m/e 814 (M+H)$^+$.

EXAMPLE 61

N-(7-Aminoheptanoyl)-{(2S)-2-Amino-3-cyclohexylpropanoyl}-Sarconsinyl-Leucyl-{(R/S)-2-Amino-5-phenylpentanoyl}-Arginyl-OH MS (FAB) m/e 814 (M+H)$^+$. Amino Acid Analysis: Cha (0.90), Sar (1.10), Leu (1.02), Arg (1.01).

EXAMPLE 62

N-(5-Phenylvaleryl)-{(2S)-2-Amino-3-cyclohexylpropanoyl}-Glycyl-Leucyl-{(R)-2-Amino-5-phenylpentanoyl}-Arginyl-OH MS (FAB) m/e 833 (M+H)$^+$. Amino Acid Analysis: Cha (0.88), Gly (0.98), Leu (1.02), Arg (1.00).

EXAMPLE 63

H-{(2S)-2-Amino-3-cyclohexylpropanoyl}(N-Benzyl)-Glycyl-Leucyl-{(R)-2-Amino-5-phenylpentanoyl}-Arginyl-OH MS (FAB) m/e 763 (M+H)$^+$. Amino Acid Analysis: Gly (0.94), Leu (1.04), Arg (1.02).

EXAMPLE 64

N-(7-Aminoheptanoyl)-{(2S)-2-Amino-3-cyclohexylpropanoyl}(N-Benzyl)-Glycyl-Leucyl-{(R)-2-Amino-5-phenylpentanoyl}-Arginyl-OH MS (FAB) m/e 890 (M+H)$^+$.

EXAMPLE 65

N-[(1,2-Dihydro-3H-indol-3-ylidine)-acetyl]-Glycyl-Leucyl-{(R)-2-Amino-5-phenylpentanoyl}-Arginyl-OH MS (FAB) m/e 677 (M+H)$^+$. Amino Acid Analysis: Gly (1.01), Leu (1.02), Arg (0.97).

EXAMPLE 66

N-[(1,2-Dihydro-3H-indol-3-ylidine)-acetyl]-Glycyl-Leucyl-{(R)-2-Amino-5-phenylpentanoyl}-Arginyl-OH MS (FAB) m/e 677 (M+H)$^+$. Amino Acid Analysis: Gly (1.01), Leu (1.02), Arg (0.97).

EXAMPLE 67

H-Glycyl-Lysyl-Prolyl-{(2S)-2-Amino-3-cyclohexylpropanoyl}-Alanyl-Leucyl-{(R)-2-Amino-4-butyryl}-Arginyl-OH MS (FAB) m/e 955 (M+H)$^+$. Amino Acid Analysis: Gly (0.95), Lys (0.99), Pro (0.95), Cha (0.98), Ala (0.99), Leu (1.05), Arg (1.06).

EXAMPLE 68

H-Lysyl-Prolyl-{(2S)-2-Amino-3-cyclohexylpropanoyl}-Alanyl-Leucyl-{(R/S)-2-Amino-5-phenylpentanoyl}-Arginyl-OH MS (FAB) m/e 912 (M+H)$^+$.

EXAMPLE 69

H-Lysyl-Prolyl-{(2S)-2-Amino-3-cyclohexylpropanoyl}-Alanyl-Leucyl-{(R/S)-2-Amino-5-phenylpentanoyl}-Arginyl-OH MS (FAB) m/e 912 (M+H)$^+$. Amino Acid Analysis: Lys (0.91), Pro (0.95), Ala (0.90), Leu (1.01), Arg (1.10).

EXAMPLE 70

N-(6-Aminohexanoyl)-{(2S)-2-Amino-3-cyclohexylpropanoyl}-Glycyl-Leucyl-{(R/S)-2-Amino-5-phenylpentanoyl}-Arginyl-OH MS (FAB) m/e 786 (M+H)+.

EXAMPLE 71

N-(6-Aminohexanoyl)-{(2S)-2-Amino-3-cyclohexylpropanoyl}-Glycyl-Leucyl-{(R/S)-2-Amino-5-phenylpentanoyl}-Arginyl-OH MS (FAB) m/e 786 (M+H)+. Amino Acid Analysis: Cha (0.89), Gly (1.10), Leu (1.01), Arg (0.97).

EXAMPLE 72

H-Glycyl-{(2S)-2-Amino-3-cyclohexylpropanoyl}-Glycyl-Leucyl-{(R/S)-2-Amino-5-phenylpentanoyl}-Arginyl-OH MS (FAB) m/e 730 (M+H)+.

EXAMPLE 73

H-Glycyl-{(2S)-2-Amino-3-cyclohexylpropanoyl}-Glycyl-Leucyl-{(R/S)-2-Amino-5-phenylpentanoyl}-Arginyl-OH MS (FAB) m/e 730 (M+H)+. Amino Acid Analysis: Gly (2.08), Cha (0.92); Leu (1.02), Arg (0.98).

EXAMPLE 74

N-(6-Aminohexanoyl)-{(2S)-2-Amino-3-cyclohexylpropanoyl}-Glycyl-Alanyl-{(+)-2-Amino-5-phenylpentanoyl}-Arginyl-OH MS (FAB) m/e 744 (M+H)+. Amino Acid Analysis Cha (1.03), Gly (0.81), Ala (0.99), Arg (1.10).

EXAMPLE 75

N-(7-Aminoheptanoyl)-{(2S)-2-Amino-3-cyclohexylpropanoyl}(N-methyl)-Glycyl-Leucyl-{(R/S)-2-Amino-5-phenylpentanoyl}-Arginyl-OH MS (FAB) m/e 814 (M+H)+.

EXAMPLE 76

N-(7-Aminoheptanoyl)-{(2S)-2-Amino-3-cyclohexylpropanoyl}(N-methyl)-Glycyl-Leucyl-{(R/S)-2-Amino-5-phenylpentanoyl}-Arginyl-OH MS (FAB) m/e 814 (M+H)+. Amino Acid Analysis: Gly (0.96), Leu (0.98), Arg (1.06).

EXAMPLE 77

N-(3-Phenylpropyl)-{(2S)-2-Amino-3-cyclohexylpropanoyl}-Glycyl-Leucyl-{(R)-2-Amino-5-phenylpentanoyl}-Arginyl-OH MS (FAB) m/e 791 (M+H)+. Amino Acid Analysis: Gly (0.94), Leu (1.02), Arg (1.04).

EXAMPLE 78

N-(2-Phenethyl)-{(2S)-2-Amino-3-cyclohexylpropanoyl}-Glycyl-Leucyl-{(R)-2-Amino-5-phenylpentanoyl}-Arginyl-OH MS (FAB) m/e 777 (M+H)+. Amino Acid Analysis: Gly (0.93), Leu (1.03), Arg (1.04).

EXAMPLE 79

N-[(Indol-3-yl)ethyl]-Glycyl-Leucyl-{(R)-2-Amino-5-phenylpentanoyl}-Arginyl-OH

MS (FAB) m/e 663 (M+H)+,

EXAMPLE 80

N-[(Indoline-3-yl)acetyl]-Glycyl-Leucyl-{(R)-2-Amino-5-phenylpentanoyl}-Arginyl-OH MS (FAB) role 679 (M+H)+.

EXAMPLE 81

N-(6-Aminohexanoyl)-Prolyl-{(2S)-2-Amino-3-cyclohexylpropanoyl}-Alanyl-Leucyl-{(+)-2-Amino-5-phenylpentanoyl}-Arginyl-OH MS (FAB) m/e 897 (M+H)+. Amino Acid Analysis: Pro (1.00), Cha (1.00), Ala (0.85), Leu (1.00), Arg (1.08).

EXAMPLE 82

N-(6-Aminohexanoyl)-Prolyl-{(2S)-2-Amino-3-cyclohexylpropanoyl}-Alanyl-Leucyl-{(±)-2-Amino-5-phenylpentanoyl}-Arginyl-OH MS (FAB) m/e 897 (M+H)+.

EXAMPLE 83

N-(8-Aminocaproyl)-{(2S)-2-Amino-3-cyclohexylpropanoyl}-Glycyl-Leucyl-{(R/S)-2-Amino-5-phenylpentanoyl}-Arginyl-OH MS (FAB) m/e 814 (M+H)+. Amino Acid Analysis: Cha (0.84), Gly (1.10), Leu (0.95), Arg (0.92).

EXAMPLE 84

H-β-Alanyl-{(2S)-2-Amino-3-cyclohexylpropanoyl}-Glycyl-Leucyl-{(R/S)-2-Amino-5-phenylpentanoyl}-Arginyl-OH MS (FAB) m/e 744 (M+H)+.

EXAMPLE 85

H-β-Alanyl-{(2S)-2-Amino-3-cyclohexylpropanoyl}-Glycyl-Leucyl-{(R/S)-2-Amino-5-phenylpentanoyl}-Arginyl-OH MS (FAB) m/e 744 (M+H)+. Amino Acid Analysis: Cha (0.90), Gly (0.95), Leu (1.07), Arg (1.01).

EXAMPLE 86

N-(6-Aminohexanoyl)-{(2S)-2-Amino-3-cyclohexylpropanoyl}-Leucyl-{(R/S)-2-Amino-5-phenylpentanoyl}-Arginyl-OH MS (FAB) m/e 729 (M+H)+.

EXAMPLE 87

N-(6-Aminohexanoyl)-{(2S)-2-Amino-3-cyclohexylpropanoyl}-Leucyl-{(R/S)-2-Amino-5-phenylpentanoyl}-Arginyl-OH MS (FAB) m/e 729 (M+H)+. Amino Acid Analysis: Cha (0.90), Leu (1.02), Arg (0.98).

EXAMPLE 88

N-(6-Aminohexanoyl)-Leucyl-Glycyl-Leucyl-{(R/S)-2-Amino-5-phenylpentanoyl}-Arginyl-OH MS (FAB) m/e 81 4 (M+H)$^+$.

EXAMPLE 89

N-(6-Aminohexanoyl)-Leucyl-Glycyl-Leucyl-{(R/S)-2-Amino-5-phenylpentanoyl}-Arginyl-OH MS (FAB) m/e 814 (M+H)$^+$. Amino Acid Analysis: Leu (1.98), Gly (0.82), Arg (1.10).

EXAMPLE 90

H-Cysteinyl(S-benzyl)-Glycyl-Leucyl-{(R)-2-Amino-5-phenylpentanoyl}-Arginyl-OH

MS (FAB) m/e 713 (M+H)$^+$. Amino Acid Analysis: Gly (0.97), Leu (1.03), Arg (1.00).

EXAMPLE 91

H-Cysteinyl(S-1-phenethyl)-Glycyl-Leucyl-{(R)-2-Amino-5-phenylpentanoyl}-Arginyl-OH MS (FAB) m/e 727 (M+H)$^+$. Amino Acid Analysis: Gly (0.96),.Leu (1.02), Arg (1.02).

EXAMPLE 92

N-(3-Phenylpropanoyl)-Glycyl-Leucyl-{(R)-2-Amino-5-phenylpentanoyl}-Arginyl-OH

MS (FAB) m/e 652 (M+H)$^+$.

EXAMPLE 93

N-Phenylacetyl-Glycyl-Leucyl-{(R)-2-Amino-5-phenylpentanoyl}-Arginyl-OH

MS (FAB) m/e 638 (M+H)$^+$.

EXAMPLE 94

H-Phenylalanyl-Lysyl-Glycyl(N-benzyl)-{(R/S)-2-Amino-5-phenylpentanoyl}-Arginyl-OH MS (FAB) m/e 772 (M+H)$^+$.

EXAMPLE 95

H-Phenylalanyl-Lysyl-Glycyl(N-benzyl)-{(R/S)-2-Amino-5-phenylpentanoyl}-Arginyl-OH MS (FAB) m/e 772 (M+H)$^+$.

EXAMPLE 96

H-{(2S)-2-Amino-3-cyclohexylpropanoyl}-Lysyl-Leucyl-{(R/S)-2-Amino-5-phenylpentanoyl}-Arginyl-OH MS (FAB) m/e 744 (M+H)$^+$.

EXAMPLE 97

H-{(2S)-2-Amino-3-cyclohexylpropanoyl}-Lysyl-Leucyl-{(R/S)-2-Amino-5-phenylpentanoyl}-Arginyl-OH MS (FAB) m/e 744 (M+H)$^+$. Amino Acid Analysis: Cha (0.91), Lys (0.91), Leu (1.08), Arg (1.06).

EXAMPLE 98

H-{(2S)-2-Amino-3-cyclohexylpropanoyl}-DLysyl-Leucyl-{(R/S)-2-Amino-5-phenylpentanoyl}-Arginyl-OH MS (FAB) m/e 744 (M+H)$^+$. Amino Acid Analysis: Cha (0.96), Lys (0.98), Leu (1.08), Arg (0.98).

EXAMPLE 99

N-(6-Aminohexanoyl)-{(2S)-2-Amino-3-cyclohexylpropanoyl}-Glycyl-DLeucyl-{(R/S)-2-Amino-5-phenylpentanoyl}-Arginyl-OH MS (FAB) m/e 786 (M+H)$^+$. Amino Acid Analysis: 0ha (0.99), Gly (1.02), Leu (1.06), Arg (0.92).

EXAMPLE 100

N-(6-Aminohexanoyl)-{(2S)-2-Amino-3-cyclohexylpropanoyl}-Glycyl-DLeucyl-{(R/S)-2-Amino-5-phenylpentanoyl}-Arginyl-OH MS (FAB) m/e 786 (M+H)$^+$.

EXAMPLE 101

N-(6-Aminohexanoyl)-{(2S)-2-Amino-3-cyclohexylpropanoyl}-Glycyl-Valyl-{(R/S)-2-Amino-5-phenylpentanoyl}-Arginyl-OH MS (FAB) m/e 772 (M+H)$^+$.

EXAMPLE 102

N-(6-Aminohexanoyl)-{( 2S)-2-Amino-3-cyclohexylpropanoyl}-Glycyl-Valyl-{(FFS)-2-Amino-5-phenylpentanoyl}-Arginyl-OH MS (FAB) m/e 772 (M+H)$^+$. Amino Acid Analysis: Cha (0.94), Gly (0.90), Val (1.03), Arg (1.07).

EXAMPLE 103

N-(3-Phenylpropyl)-N-methyl-{(2S)-2-Amino-3-cyclohexylpropanoyl}-Glycyl-Leucyl-{(R)-2-Amino-5-phenylpentanoyl}-Arginyl-OH MS (FAB) m/e 805 (M+H)$^+$. Amino Acid Analysis: Gly (0.90), Leu (1.05), Arg (1.05).

EXAMPLE 104

H-{(R/S)-2-Amino-5-phenylpentanoyl}-Glycyl-Leucyl-{(R)-2-Amino-5-phenylpentanoyl}-Arginyl-OH MS (FAB) m/e 695 (M+H)$^+$. Amino Acid Analysis: Gly (1.04), Leu (1.03), Arg (1.02).

EXAMPLE 105

H-{(R/S)-2-Amino-5-phenylpentanoyl}-Glycyl-Leucyl-{(R)-2-Amino-5-phenylpentanoyl}-Arginyl-OH MS (FAB) m/e 695 (M+H)$^+$. Amino Acid Analysis: Gly (1.04), Leu (1.05), Arg (1.03).

EXAMPLE 106

N-(2-Aminocinnamoyl)-Glycyl-Leucyl-{(R)-2-Amino-5-phenylpentanoyl}-Arginyl-OH

MS (FAB) m/e 665 (M+H)$^+$.

EXAMPLE 107

N-(2-Nitrocinnamoyl)-Glycyl-Leucyl-{(R)-2-Amino-5-phenylpentanoyl}-Arginyl-OH

MS (FAB) m/e 695 (M+H)$^+$.

EXAMPLE 108

H-Glycyl-Lysyl-Prolyl-{(2S)-2-Amino-3-cyclohexylpropanoyl}-Alanyl-Leucyl-Cysteinyl(S-benzyl)-Arginyl-OH MS (FAB) m/e 987 (M+H)$^+$. Amino Acid Analysis: Gly (1.00), Lys (1.00), Pro (1.00), Cha (0.80), Ala (1.00), Leu (1.00), Arg (1.00).

EXAMPLE 109

N-(6-Aminohexanoyl)-Prolyl-{(2S)-2-Amino-3-cyclohexylpropanoyl}-(3-Aminomethylbenzoyl)-{(+)-2-Amino-5-phenylpentanoyl}-Arginyl-OH MS (FAB) m/e 846 (M+H)$^+$. Amino Acid Analysis: Pro (0.90), Cha (1.03), Arg (1.10).

EXAMPLE 110

N-(6-Aminohexanoyl)-Glycyl-{(2S)-2-Amino-3-cyclohexylpropanoyl}-Prolyl-Leucyl-{(R/S)-2-Amino-5-phenylpentanoyl}-Arginyl-OH MS (FAB) m/e 883 (M+H)$^+$.

EXAMPLE 111

N-(6-Aminohexanoyl)-Glycyl-{(2S)-2-Amino-3-cyclohexylpropanoyl}-Prolyl-Leucyl-{(R/S)-2-Amino-5-phenylpentanoyl}-Arginyl-OH MS (FAB) m/e 883 (M+H)$^+$. Amino Acid Analysis: Gly (1.00), Cha (0.90), Pro (1.00), Leu (1.00).

EXAMPLE 112

N-(gamma-Aminobutyryl)-Sarcosinyl-{(2S)-2-Amino-3-cyclohexylpropanoyl}-Glycyl-Leucyl-{(R/S)-2-Amino-5-phenylpentanoyl}-Arginyl-OH MS (FAB) m/e 829 (M+H)$^+$.

EXAMPLE 113

N-(gamma-Aminobutyryl)-Sarcrosinyl-{(2S)-2-Amino-3-cyclohexyl-propanoyl}-Glycyl-Leucyl-{(R/S)-2-Amino-5-phenylpentanoyl}-Arginyl-OH MS (FAB) m/e 829 (M+H)$^+$. Amino Acid Analysis: Gaba (0.95), Sar (1.25), Cha (0.94), Gly (0.99), Leu (1.07), Arg (0.94).

EXAMPLE 114

N-(6-Aminohexanoyl)-{(2S)-2-Amino-3-cyclohexylpropanoyl}-beta-Alanyl-Leucyl-{(R/S)-2-Amino-5-phenylpentanoyl}-Arginyl-OH MS (FAB) m/e 800 (M+H)$^+$.

EXAMPLE 115

N-(6-Aminohexanoyl)-{(2S)-2-Amino-3-cyclohexylpropanoyl}-beta-Alanyl-Leucyl-{(R/S)-2-Amino-5-phenylpentanoyl}-Arginyl-OH MS (FAB) m/e 800 (M+H)$^+$. Amino Acid Analysis: Cha (0.96), Leu (0.93), Arg (1.07).

EXAMPLE 116

H-Phenylalanyl-Glycyl-Leucyl-{(R)-2-Amino-5-phenylpentanoyl}-Arginyl-OH

MS (FAB) m/e 667 (M+H)$^+$. Amino Acid Analysis: Phe (1.03), Gly (1.03), Leu (1.04), Arg (1.02).

EXAMPLE 117

H-{(S)-2-Amino-4-phenylbutyryl}-Glycyl-Leucyl-{(R)-2-Amino-5-phenylpentanoyl}-Arginyl-OH MS (FAB) m/e 681 (M+H)$^+$. Amino Acid Analysis: hPhe (0.97), Gly (1.03), Leu (1.04), Arg (1.02).

EXAMPLE 118

N-(6-Aminohexanoyl)-Sarcosinyl-{(2S)-2-Amino-3-cyclohexylpropanoyl}-Alanyl-Leucyl-{(R/S)-2-Amino-5-phenylpentanoyl}-Arginyl-OH MS (FAB) m/e 871 (M+H)$^+$.

EXAMPLE 119

H-Lysyl-Glycyl-{(2S)-2-Amino-3-cyclohexylpropanoyl}-Glycyl-Leucyl-{(R/S)-2-Amino-5-phenylpentanoyl}-Arginyl-OH MS (FAB) m/e 858 (M+H)$^+$.

EXAMPLE 120

N-(6-Aminohexanoyl)-Sercosinyl-{(2S)-2-Amino-3-cyclohexylpropanoyl}-Alanyl-Leucyl-{(R/S)-2-Amino-5-phenylpentanoyl}-Arginyl-OH MS (FAB) m/e 871 (M+H)$^+$. Amino Acid Analysis: Sar (1.10), Cha (0.90), Ala (0.93), Leu (1.00), Arg (0.98).

EXAMPLE 121

N-(6-Aminohexanoyl)-{(2S)-2-Amino-3-cyclohexylpropanoyl}-Alanyl-Leucyl-{(R/S)-2-Amino-5-phenylpentanoyl}-Arginyl-OH MS (FAB) m/e 800 (M+H)$^+$. Amino Acid Analysis: Cha (1.02), Ala (1.00), Leu (0.91), Arg (1.00).

EXAMPLE 122

N-(7-Aminoheptanoyl)-{(2S)-2-Amino-3-cyclohexylpropanoyl}-Glycyl-Leucyl-{(R/S)-2-Amino-5-phenylpentanoyl}-Arginyl-OH MS (FAB) m/e 800 (M+H)$^+$.

EXAMPLE 123

N-(7-Aminoheptanoyl)-{(2S)-2-Amino-3-cyclohexylpropanoyl}-Glycyl-Leucyl-{(R/S)-2-Amino-5-phenylpentanoyl}-Arginyl-OH MS (FAB) role 800 (M+H)$^+$. Amino Acid Analysis: Cha (0.81), Gly (0.99), Leu (1.00), Arg (1.00).

EXAMPLE 124

N-(6-Aminohexanoyl)-Phenylalanyl-Glycyl-Leucyl{(R/S)-2-Amino-5-phenylpentanoyl}-Arginyl-OH MS (FAB) m/e 780 (M+H)$^+$.

EXAMPLE 125

N-(6-Aminohexanoyl)-Phenylalanyl-Glycyl-Leucyl-{(R/S)-2-Amino-5-phenylpentanoyl}-Arginyl-OH MS (FAB) role 780 (M+H)$^+$. Amino Acid Analysis: Phe (1.05), Gly (0.90), Leu (1.09), Arg (0.96).

EXAMPLE 126

N-(6-Aminohexanoyl)-{(2S)-2-Amino-3-cyclohexylpropanoyl}-DAlanyl-Leucyl-{(R/S)-2-Amino-5-phenylpentanoyl}-Arginyl-OH MS (FAB) m/e 800 (M+H)$^+$. Amino Acid Analysis: Cha (0.90), Ala (1.05), Leu (1.07), Arg (1.07).

EXAMPLE 127

N-(6-Aminohexanoyl)-{(2S)-2-Amino-3-cyclohexylpropanoyl}-DAlanyl-Leucyl,{(R/S)-2-Amino-5-phenylpentanoyl}-Arginyl-OH MS (FAB) m/e 800 (M+H)$^+$.

EXAMPLE 128

(N-Methyl)-Phenylalanyl-Lysyl-Prolyl-{(2S)-2-Amino-3-cyclohexylpropanoyl}-Alanyl-Leucyl-{(R/S)-2-Amino-5-phenylpentanoyl}-Arginyl-OH MS (FAB) m/e 1073 (M+H)$^+$. NMePhe (0.92), Lys (0.90), Pro (0.98), Cha (0.95), Ala (0.92), Leu (1.05), Arg (1.05).

EXAMPLE 129

(N-Methyl)-Phenylalanyl-Lysyl-Prolyl-{(2S)-2-Amino-3-cyclohexyl-propanoyl}-Alanyl-Leucyl-{(R/S)-2-Amino-5-phenylpentanoyl}-Arginyl-OH MS (FAB) m/e 1073 (M+H)$^+$. NMePhe (0.94), Lys (0.91), Pro (1.03), Cha (0.98), Ala (0.94), Leu (1.04), Arg (1.02).

EXAMPLE 130

H-Tryptophanyl-Glycyl-Leucyl-{(R)-2-Amino-5-phenylpentanoyl}-Arginyl-OH

MS (FAB) m/e 706 (M+H)$^+$. Amino Acid Analysis: Trp (0.90), Gly (1.07), Leu (1.08), Arg (1.10).

EXAMPLE 131

N-[(Indol-2-yl)-carbonyl]-Glycyl-Leucyl-{(R)-2-Amino-5-phenylpentanoyl}-Arginyl-OH MS (FAB) m/e 663 (M+H)$^+$.

EXAMPLE 132

N-(3-Cyclohexyl-2-hydroxypropionyl)-Glycyl-Leucyl-{(R)-2-Amino-5-phenylpentanoyl}-Arginyl-OH MS (FAB) m/e 674 (M+H)$^+$. Amino Acid Analysis: Gly (0.93), Leu (1.08), Arg (1.00).

EXAMPLE 133

N-(gama-Aminobutyryl)-{(2S)-2-Amino-3-cyclohexylpropanoyl}-Glycyl-Leucyl-{(R/S)-2-Amino-5-phenylpentanoyl}-Arginyl-OH MS (FAB) m/e 758 (M+H)$^+$.

EXAMPLE 134

N-(gama-Aminobutyryl)-{(2S)-2-Amino-3-cyclohexylpropanoyl}-Glycyl-Leucyl-{(R/S)-2-Amino-5-phenylpentanoyl}-Arginyl-OH MS (FAB) m/e 758 (M+H)$^+$. Amino Acid Analysis: Cha (0.89), Gly (1.10), Leu (1.09), Arg (1.03).

EXAMPLE 135

N-(6-Aminohexanoyl)-{(2S)-2-Amino-3-cyclohexylpropanoyl}-Alanyl-Leucyl-{(R/S)-2-Amino-5-phenylpentanoyl}-Arginyl-OH MS (FAB) m/e 800 (M+H)$^+$. Amino Acid Analysis: Cha (0.84), Ala (0.98), Leu (1.06), Arg (0.96).

EXAMPLE 136

N-(6-Aminohexanoyl)-{(2S)-2-Amino-3-cyclohexylpropanoyl}-Glycyl-Leucyl-{(R/S)-2-Amino-5-phenylpentanoyl}-Arginyl-OH MS (FAB) m/e 800 (M+H)$^+$. Amino Acid Analysis: Cha (1.02), Ala (01.01), Leu (0.91), Arg (1.00).

EXAMPLE 137

N-(6-Aminohexenoyl)-{(2S)-2-Amino-4-cyclohexylbutanoyl}-Glycyl-Leucyl-{(R/S)-2-Amino-5-phenylpentanoyl}-Arginyl-OH MS (FAB) m/e 800 (M+H)$^+$.

EXAMPLE 138

N-(6-Aminohexanoyl)-{(2S)-2-Amino-4-cyclohexylbutanoyl}-Glycyl-Leucyl-{(R/S)-2-Amino-5-phenylpentanoyl}-Arginyl-OH MS (FAB) m/e 800 (M+H)$^+$.

EXAMPLE 139

N-(5-Aminopentanoyl)-{(2S)-2-Amino-3-Cyclohexylpropanoyl}-Glycyl-Leucyl-{(R/S)-2-Amino-5-phenylpentanoyl}-Arginyl-OH MS (FAB) m/e 772 (M+H)$^+$. Amino Acid Analysis: Cha (0.89), Gly (0.99), Leu (1.10), Arg (1.04).

EXAMPLE 140

N-(5-Aminopentanoyl)-{(2S)-2-Amino-3-cyclohexylpropanoyl}-Glycyl-Leucyl-{(R/S)-2-Amino-5-phenylpentanoyl}-Arginyl-OH MS (FAB) m/e 772 (M+H)$^+$.

EXAMPLE 141

N-[N-(3-Aminomethylbenzyl)aminocarbonyl]-{(2S)-2-Amino-3-cyclohexylpropanoyl}-Glycyl-Leucyl-{(R/S)-2-Amino-5-phenylpentanoyl}-Arginyl-OH MS (FAB) m/e 835 (M+H)$^+$.

EXAMPLE 142

N-[N-(3-Aminomethylbenzyl)aminocarbonyl]-{(2S)-2-Amino-3-cyclohexylpropanoyl}-Glycyl-Leucyl-{(R/S)-2-Amino-5-phenylpentanoyl}-Arginyl-OH MS (FAB) m/e 835 (M+H)$^+$. Amino Acid Analysis: Gly (1.00), Leu (1.02), Arg (1.07).

EXAMPLE 143

H-Phenylalanyl-Alanyl-Prolyl-{(2S)-2-Amino-3-cyclohexylpropanoyl}-Alanyl-Leucyl-{(±)-2-Amino-5-phenylpentanoyl}-Arginyl-OH MS (FAB) m/e 1002 (M+H)⁺. Amino Acid Analysis: Phe (1.00), Ala (1.93), Pro (1.04), Cha (0.90), Leu (1.05), Arg (1.04).

EXAMPLE 144

N-(6-Aminohexanoyl)-{(2S)-2-Amino-3-cyclohexylpropanoyl}-(3-Aminomethylbenzoyl)-{(+)-2-Amino-5-phenylpentanoyl}-Arginyl-OH MS (FAB) m/e 1002 (M+H)⁺. Amino Acid Analysis: Cha (0.93), Arg (1.07).

EXAMPLE 145

N-[N-(4-Aminomethylbenzyl)aminocarbonyl]-{(2S)-2-Amino-3-cyclohexylpropanoyl}-Glycyl-Leucyl-{(R/S)-2-Amino-5-phenylpentanoyl}-Arginyl-OH MS (FAB) m/e 835 (M+H)⁺. Amino Acid Analysis: Gly (0.98), Leu (1.02), Arg (1.05).

EXAMPLE 146

N-(Benzoyl)-Leucyl-{(R/S)-2-Amino-5-phenylpentanoyl}-Arginyl-OH

MS (FAB) m/e 567 (M+H)⁺.

EXAMPLE 147

H-(4-Pyridyl)alanyl-Lysyl-Prolyl-{(2S)-2-Amino-3-cyclohexylpropanoyl}-Alanyl-Leucyl-{(R)-2-Amino-5-phenylpentanoyl}-Arginyl-OH The title compound is prepared using the methods described in Examples 1 and 2.

EXAMPLE 148

H-Phenylalanyl-Lysyl-Alanyl-{(2S)-2-Amino-3-cyclohexylpropanoyl}-Alanyl-(Indol-3-yl)alanyl{(R/S)-2-Amino-5-phenylpentanoyl}-Arginyl-OH The title compound is prepared using the methods described in Examples 1 and 2.

EXAMPLE 149

N-(6-Aminohexanoyl)-(2-Thienyl)alanyl(N-methyl)-Glycyl-Leucyl-{(R/S)-2-Amino-5-phenylpentanoyl}-Arginyl-OH The title compound is prepared using the methods described in Examples 1 and 2.

EXAMPLE 150

H-Phenylalanyl-Lysyl-Alanyl-{(2S)-2-Amino-4-(morpholinyl)butanoyl}-Alanyl-Phenylalanyl{(R/S)-2-Amino-5-phenylpentanoyl}-Arginyl-OH The title compound is prepared using the methods described in Examples 1 and 2.

The foregoing examples are merely illustrative of the invention and are not intended to limit the invention to the disclosed compounds. Variations and changes which are obvious to one skilled in the art are intended to be within the scope and nature of the invention, which is defined in the appended Claims.

What is claimed is:

1. A compound of the formula:

A-B-D-E-G-J-L-M-N(R⁴) Arg-OH or a pharmaceutically-acceptable salt thereof, wherein A is $R^1$–$R^2$, hydrogen, $C_1$–$C_8$-alkyl, aryl-$C_1$–$C_6$-alkyl, amino-$C_1$–$C_8$-alkyl, guanidino-$C_1$–$C_8$-alkyl, amino-$C_1$–$C_8$-alkyl-C(O)— or guanidino-$C_1$–$C_8$-alkyl-C(O)—, with the proviso that when none of the optionally-present residues, B, D, E, G and J, is absent, A is hydrogen or methyl;

B is absent or —N($R^4$)—C($R^5$)($R^6$)—$R^3$—;

D is absent or —N($R^4$)—C($R^7$)($R^8$—$R^3$—;

E is absent or —N ($R^4$)—C($R^9$)($R^{10}$)—$R^3$—, or $R^{20}$, or when either residue B or residue D is absent, $R^{19}$;

G is absent or —N($R^4$)—C($R^{11}$)($R^{12}$)—$R^3$—;

J is absent or —N($R^{21}$)—C($R^{13}$)($R^{14}$)—$R^3$—, or $R^{20}$;

L is —N($R^4$)—C($R^{15}$)($R^{16}$)—C(O)—; and

M is—N($R^4$)—C($R^{17}$)($R^{18}$)—C(O)—, where $R^1$ is $C_1$–$C_8$-alkyl, aryl, aryl-$C_1$–$C_8$-alkyl, amino-$C_1$–$C_8$-alkyl, (heterocyclic)-$C_1$–$C_6$-alkyl or hydrogen, with the proviso that when $R^2$ is >SO₂, then $R^1$ may not be hydrogen;

$R^2$ is >C=O, >CH₂, —NH—C(O)— or >SO₂;

$R^3$ is >C=O, >CH₂, or —CH₂—C(O)—;

$R^4$ is hydrogen, $C_1$–$C_8$-alkyl or aryl—$C_1$–$C_6$-alkyl;

$R^5$, $R^7$, $R^9$, $R^{11}$, $R^{13}$, $R^{15}$, and $R^{17}$ are independently hydrogen or $C_1$–$C_8$-alkyl;

$R^6$ is hydrogen, $C_1$–$C_8$-alkyl, aryl, aryl-$C_1$–$C_6$-alkyl or (heterocyclic)-$C_1$–$C_6$-alkyl;

$R^8$ is hydrogen, $C_1$–$C_8$-alkyl, amino-$C_1$–$C_8$-alkyl, or guanidino-$C_1$–$C_8$-alkyl;

$R^{10}$ is selected from the group consisting of hydrogen, $C_1$–$C_8$-alkyl, aryl, aryl-$C_1$–$C_6$-alkyl, amino-$C_1$–$C_8$-alkyl, amino(cyclo-$C_3$–$C_6$-alkyl), amido-$C_1$–$C_8$-alkyl, hydroxy-$C_1$–$C_8$-alkyl, guanidino-$C_1$–$C_8$-alkyl and carboxy-$C_1$–$C_8$-alkyl;

$R^{12}$ is selected from the group consisting of hydrogen, sulfhydryl-$C_1$–$C_8$-alkyl, (thio-$C_1$–$C_8$-alkoxy)-$C_1$–$C_8$-alkyl, $C_1$–$C_8$-alkyl, aryl, aryl-$C_1$–$C_6$-alkyl, (cyclo-$C_3$–$C_8$-alkyl)-$C_1$–$C_8$-alkyl and (heterocyclic)-$C_1$–$C_6$-alkyl;

$R^{14}$ is selected from the group consisting of hydrogen, $C_1$–$C_8$-alkyl, amino-$C_1$–$C_8$-alkyl, aryl, aryl-$C_1$–$C_8$-alkyl, (cyclo-$C_3$–$C_6$-alkyl)-$C_1$–$C_8$-alkyl, (carboxamido)-$C_1$–$C_8$-alkyl and (heterocyclic)-$C_1$–$C_6$-alkyl;

$R^{16}$ is hydrogen, $C_1$–$C_8$-alkyl, aryl, aryl-$C_1$–$C_6$-alkyl, (cyclo-$C_3$–$C_6$-alkyl)-$C_1$–$C_8$-alkyl or (heterocyclic)-$C_1$–$C_6$-alkyl;

$R^{18}$ is selected from the group consisting of (a) —(CH₂)₃-(aryl), (b) —CH₂—W—CH₂-(aryl), where W is selected from >O, >S, and >N—R, where R is hydrogen or $C_1$–$C_8$-alkyl, and (c) —CH₂—CH₂—W-(aryl), where W is as defined above;

R$^{19}$ is

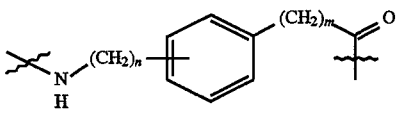

where m and n are integers independently selected from 0, 1 and 2;

R$^{20}$ is

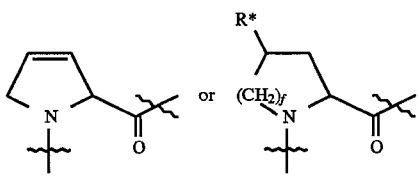

where f is 1 or 2, R* is hydrogen, hydroxy, C$_1$–C$_8$-alkoxy or aryl-C$_1$–C$_8$-alkoxy; and R$^{21}$ is hydrogen or C$_1$–C$_8$-alkyl.

2. A compound as defined in claim 1, wherein R$^3$ is >C=O or >CH$_2$.

3. A compound as defined in claim 1, wherein R$^4$ is hydrogen or methyl.

4. A compound as defined in claim 1, wherein M is 2-amino-5-phenylpentanoyl.

5. A compound as defined in claim 4, wherein the chirality of the 2-amino-5-phenylpentanoyl group is R.

6. A compound as defined in claim 1, selected from the group consisting of

H-Phenylalanyl-Lysyl-Prolyl-{(2S)-2-Amino-3-cyclohexylpropanoyl}-Alanyl-Leucyl-{(R/S)-2-Amino-5-phenyl-pentanoyl}-Arginyl-OH;

H-Phenylalanyl-Lysyl(N-epsilon-Cbz)-Prolyl-{(2S)-2-Amino-3-cyclohexylpropanoyl}-Alanyl-Leucyl-{(R/S)-2-Amino-5-phenylpentanoyl}-Arginyl-OH;

H-Phenylalanyl-Lysyl-Alanyl-{(2S)-2-Amino-3-cyclohexylpropanoyl}-Alanyl-DPhenylalanyl-{(R/S)-2-Amino-5-phenylpentanoyl}-Arginyl-OH;

H-Phenylalanyl-Lysyl-Alanyl-{(2S)-2-Amino-3-cyclohexylpropanoyl}-Alanyl-DPhenylalanyl-{(R/S)-2-Amino-5-phenylpentanoyl}-Arginyl-OH;

H-Lysyl-Glycyl-{(2S)-2-Amino-3-cyclohexylpropanoyl}-Glycyl-Leucyl-{(R/S)-2-Amino-5-phenylpentanoyl}-Arginyl-OH;

H-Phenylalanyl-Lysyl-Alanyl-{(2S)-2-Amino-3-cyclohexylpropanoyl}-Alanyl-Phenylalanyl-{(R/S)-2-Amino-5-phenylpentanoyl}-Arginyl-OH;

H-Phenylalanyl-Lysyl-Alanyl-{(2S)-2-Amino-3-cyclohexylpropanoyl}-Alanyl-Phenylalanyl-{(R/S)-2-Amino-5-phenylpentanoyl}-Arginyl-OH;

H-{(2S)-2-Amino-3-cyclohexylpropanoyl}-Alanyl-Leucyl-{(R)-2-Amino-5-phenylpentanoyl}-Arginyl-OH;

N-(6-Aminohexanoyl)-Phenylalanyl(N-methyl)-Glycyl-Leucyl-{(R/S)-2-Amino-5-phenylpentanoyl}-Arginyl-OH;

N-(7-Aminoheptanoyl)-{(2S)-2-Amino-3-cyclohexylpropanoyl}-Glycyl-Leucyl(N-methyl)-{(R/S)-2-Amino-5-phenylpentanoyl}-Arginyl-OH;

N-(7-Aminoheptanoyl)-{(2S)-2-Amino-3-cyclohexylpropanoyl}-Glycyl-Leucyl-{(R/S)-2-Amino-5-phenylpentanoyl}(N-methyl)-Arginyl-OH;

N-(6-Aminohexanoyl)-Glycyl-{(2S)-2-Amino-3-cyclohexylpropanoyl}-Alanyl-Leucyl-{(R/S)-2-Amino-5-phenylpentanoyl}-Arginyl-OH;

H-Lysyl-{(2S)-2-Amino-3-cyclohexylpropanoyl}-Glycyl-Leucyl-{(R/S)-2-Amino-5-phenylpentanoyl}-Arginyl-OH;

H-Glycyl-Lysyl-Prolyl-{(2S)-2-Amino-3-cyclohexylpropanoyl}-Alanyl-Leucyl-{(R/S)-2-Amino-5-phenylpentanoyl}-Arginyl-OH;

H-{(2S)-2-Amino-3-cyclohexylpropanoyl}-Glycyl-Leucyl-{(R/S)-2-Amino-5-phenylpentanoyl}-Arginyl-OH;

H-Lysyl-Prolyl-{(2S)-2-Amino-3-cyclohexylpropanoyl}-Alanyl-Leucyl-{(R/S)-2-Amino-5-phenylpentanoyl}-Arginyl-OH;

N-(6-Aminohexanoyl)-{(2S)-2-Amino-3-cyclohexylpropanoyl}-Glycyl-Leucyl-{(R/S)-2-Amino-5-phenylpentanoyl}-Arginyl-OH;

N-(6-Aminohexanoyl)-Prolyl-{(2S)-2-Amino-3-cyclohexylpropanoyl}-Alanyl-Leucyl-{(±)-2-Amino-5-phenylpentanoyl}-Arginyl-OH;

N-(6-Aminohexanoyl)-Prolyl-{(2S)-2-Amino-3-cyclohexylpropanoyl}-Alanyl-Leucyl-{(±)-2-Amino-5-phenyl-pentanoyl}-Arginyl-OH;

N-(8-Aminocaproyl)-{(2S)-2-Amino-3-cyclohexylpropanoyl}-Glycyl-Leucyl-{(R/S)-2-Amino-5-phenylpentanoyl}-Arginyl-OH;

N-(gamma-Aminobutyryl)-Sarcosinyl-{(2S)-2-Amino-3-cyclohexylpropanoyl}-Glycyl-Leucyl-{(R/S)-2-Amino-5-phenylpentanoyl}-Arginyl-OH;

N-(6-Aminohexanoyl)-Sarcosinyl-{(2S)-2-Amino-3-cyclohexylpropanoyl}-Alanyl-Leucyl-{(R/S)-2-Amino-5-phenylpentanoyl}-Arginyl-OH;

N-(7-Aminoheptanoyl)-{(2S)-2-Amino-3-cyclohexylpropanoyl}-Glycyl-Leucyl-{(R/S)-2-Amino-5-phenylpentanoyl}-Arginyl-OH;

N-(6-Aminohexanoyl)-Phenylalanyl-Glycyl-Leucyl{(R/S)-2-Amino-5-phenylpentanoyl}-Arginyl-OH;

N-Methyl-Phenylalanyl-Lysyl-Prolyl-{(2S)-2-Amino-3-cyclohexylpropanoyl}-Alanyl-Leucyl-{(R/S)-2-Amino 5-phenylpentanoyl}-Arginyl-OH;

N-Methyl-Phenylalanyl-Lysyl-Prolyl-{(2S)-2-Amino-3-cyclohexylpropanoyl}-Alanyl-Leucyl-{(R/S)-2-Amino-5-phenylpentanoyl}-Arginyl-OH;

N-(5-Aminopentanoyl)-{(2S)-2-Amino-3-cyclohexylpropanoyl}-Glycyl-Leucyl-{(R/S)-2-Amino-5-phenylpentanoyl}-Arginyl-OH;

N-(6-Aminohexanoyl)-{(2S)-2-Amino-3-cyclohexylpropanoyl}-(3-Aminomethylbenzoyl)-{(±)-2-Amino-5-phenylpentanoyl}-Arginyl-OH;

N-(gama-Aminobutyryl)-{(2S)-2-Amino-3-cyclohexylpropanoyl}-Glycyl-Leucyl-{(R/S)-2-Amino-5-phenylpentanoyl}-Arginyl-OH;

H-(4-Pyridyl)alanyl-Lysyl-Prolyl-{(2S)-2-Amino-3-cyclohexylpropanoyl}-Alanyl-Leucyl-{(R)-2-Amino-5-phenylpentanoyl}-Arginyl-OH;

H-Phenylalanyl-Lysyl-Alanyl{(2S)-2-Amino-3-cyclohexylpropanoyl}-Alanyl-(Indol-3-yl)alanyl-{(R/S)-2-Amino-5-phenylpentanoyl}-Arginyl-OH;

N-(6-Aminohexanoyl)-(2-Thienyl)alanyl(N-methyl)-Glycyl-Leucyl-{(R/S)-2-Amino-5-phenylpentanoyl}-Arginyl-OH; and H-Phenylalanyl-Lysyl-Alanyl-{(2S)-2-Amino-4-(Morpholinyl)butanoyl}-Alanyl-Phenylalanyl-{(R/S)-2-Amino-5-phenylpentanoyl}-Arginyl-OH.

7. A compound as defined in claim 1, selected from the group consisting of

N-(3-Phenylpropyl)-Tryptophanyl-Glycyl-Leucyl-{(R)-2-Amino-5-phenylpentanoyl}-Arginyl-OH;

H-Prolyl-{(2S)-2-Amino-3-cyclohexylpropanoyl}-Alanyl-Leucyl-{(R)-2-Amino-5-phenylpentanoyl}-Arginyl-OH;

N-(3-Phenylpropanoyl)-{(2S)-2-Amino-3-cyclohexylpropanoyl}-Glycyl-Leucyl-{(R)-2-Amino-5-phenylpentanoyl}-Arginyl-OH;

N-(Indole-3-acetyl)-Glycyl-Leucyl-{(R)-2-Amino-5-phenyl-pentanoyl}-Arginyl-OH;

N-(4-Phenylbutyryl)-{(2S)-2-Amino-3-cyclohexylpropanoyl}-Glycyl-Leucyl-{(R)-2-Amino-5-phenylpentanoyl}-Arginyl-OH;

H-{(2S)-2-Amino-3-cyclohexylpropanoyl}(N-Benzyl)-Glycyl-Leucyl-{(R)-2-Amino-5-phenylpentanoyl}-Arginyl-OH;

N-(7-Aminoheptanoyl)-{(2S)-2-Amino-3-cyclohexylpropanoyl}(N-Benzyl)-Glycyl-Leucyl-{(R)-2-Amino-5-phenylpentanoyl}-Arginyl-OH;

N-[(1,2-Dihydro-3H-indol-3-ylidine)-acetyl]-Glycyl-Leucyl-{(R)-2-Amino-5-phenylpentanoyl}-Arginyl-OH;

N-[(1,2-Dihydro-3H-indol-3-ylidine)-acetyl]-Glycyl-Leucyl-{(R)-2-Amino-5-phenylpentanoyl}-Arginyl-OH;

H-{(2S)-2-Amino-3-cyclohexylpropanoyl}(N-3-phenylpropyl)-Glycyl-Leucyl-{(R)-2-Amino-5-phenylpentanoyl}-Arginyl-OH;

H-{(2S)-2-Amino-3-cyclohexylpropanoyl}(N-2-phenethyl)-Glycyl-Leucyl-{(R)-2-Amino-5-phenylpentanoyl}-Arginyl-OH;

N-[(Indol-3-yl)ethyl]-Glycyl-Leucyl{(R)-2-Amino-5-phenylpentanoyl}-Arginyl-OH;

N-(Indoline-3-yl)acetyl]-Glycyl-Leucyl-{(R)-2-Amino-5-phenylpentanoyl}-Arginyl-OH;

H-Cysteinyl(S-benzyl)-Glycyl-Leucyl-{(R)-2-Amino-5-phenylpentanoyl}-Arginyl-OH;

H-Cysteinyl(S-1-phenethyl)-Glycyl-Leucyl-{(R)-2-Amino-5-phenyl-pentanoyl}-Arginyl-OH;

N-(3-Phenylpropanoyl)-Glycyl-Leucyl-{(R)-2-Amino-5-phenylpentanoyl}-Arginyl-OH;

N-Phenylacetyl-Glycyl-Leucyl-{(R)-2-Amino-5-phenylpentanoyl}-Arginyl-OH;

H-{(R/S)-2-Amino-5-phenylpentanoyl}-Glycyl-Leucyl-{(R)-2-Amino-5-phenylpentanoyl}-Arginyl-OH;

N-(2-Aminocinnamoyl)-Glycyl-Leucyl-{(R)-2-Amino-5-phenylpentanoyl}-Arginyl-OH;

N-(2—Nitrocinnamoyl)-Glycyl-Leucyl-{(R)-2-Amino-5-phenylpentanoyl}-Arginyl-OH;

H-Phenylalanyl-Glycyl-Leucyl-{(R)-2-Amino-5-phenylpentanoyl}-Arginyl-OH;

H-{(S)-2-Amino-4-phenylbutyryl}-Glycyl-Leucyl-{(R)-2-Amino-5-phenylpentanoyl}-Arginyl-OH;

N-[(Indol-2-yl)-carbonyl]-Glycyl-Leucyl{(R)-2-Amino-5-phenylpentanoyl}-Arginyl-OH; and N-(3-Cyclohexyl-2-hydroxypropionyl)-Glycyl-Leucyl-{(R)-2-Amino-5-phenylpentanoyl}-Arginyl-OH.

\* \* \* \* \*